United States Patent
Ishii et al.

(10) Patent No.: US 6,235,851 B1
(45) Date of Patent: May 22, 2001

(54) POLYMERIZABLE ADAMANTANE DERIVATIVES AND PROCESS FOR PRODUCING THE SAME

(75) Inventors: Yasutaka Ishii, Takatsuki; Tatsuya Nakano; Naruhisa Hirai, both of Himeji, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/214,724

(22) PCT Filed: May 12, 1998

(86) PCT No.: PCT/JP98/02085

§ 371 Date: Jan. 11, 1999

§ 102(e) Date: Jan. 11, 1999

(87) PCT Pub. No.: WO98/52902

PCT Pub. Date: Nov. 26, 1998

(30) Foreign Application Priority Data

May 23, 1997 (JP) .................................. 9-133657

(51) Int. Cl.$^7$ .................................... C08F 20/00
(52) U.S. Cl. .................. 525/440; 525/40; 560/141; 560/220; 585/252; 564/188
(58) Field of Search ................... 585/352, 252; 526/282; 525/40, 440; 560/141, 220; 502/167, 252, 152; 564/188

(56) References Cited

U.S. PATENT DOCUMENTS

| | | | |
|---|---|---|---|
| 3,356,751 | * 12/1967 | Schneider | 585/352 |
| 3,467,627 | * 9/1969 | Duling et al. | 525/440 |
| 3,518,241 | * 6/1970 | Duling et al. | 526/282 |
| 3,580,964 | * 5/1971 | Driscoll | 525/40 |
| 3,639,362 | * 2/1972 | Duling et al. | 526/282 |
| 3,944,626 | * 3/1976 | Honna et al. | 585/352 |
| 3,994,960 | * 11/1976 | Yamazaki et al. | 560/204 |

FOREIGN PATENT DOCUMENTS

| | | |
|---|---|---|
| 42-16621 | 9/1942 | (JP) . |
| 60-124608 | 7/1985 | (JP) . |
| 63-33350 | 2/1988 | (JP) . |
| 1-182303 | 7/1989 | (JP) . |
| 4-360809 | 12/1992 | (JP) . |
| 27-61980 | 7/1995 | (JP) . |
| 8-38909 | 2/1996 | (JP) . |
| 08038909 | * 2/1996 | (JP) . |

OTHER PUBLICATIONS

Vishnevskii et al, nitration of adamantane with nitrogen dioxide, Zhurnal organ, Khimii, vol. 32 ,No. 7, Jul. 1996.*
Lide, periodic table of the elements, Handbook of Chem.& Physics 1913–1995, p. 1, Jan. 1995.*
S.S. Novikov et al, "Synthesis and polymerization of unsaturated adamantane derivatives", Izvestiya Akademii Nauk SSSR, Seriya Khimicheskaya, 1977, vol. 12, p. 2765–2767.
Take–aki Mitsudo et al; J. Org. Chem., 1987, vol. 52, p. 2230–2239.
The 67$^{th}$ Spring Annual Meeting (1994) of Chemical Society of Japan "Lecture Draft II" p. 762, 3 C2 10, 6 pages.
Mitsuhiro Takeno; et al; Faculty of Engineering, Kansai University 3 pages.
Stetter et al; Chem. Ber., 92 1629 (1959).
Stetter et al; Chem. Ber., 93 226, 1161 (1960).
Smith et al; J. Org. Chem., 26 2207 (1961).

* cited by examiner

Primary Examiner—Paul J. Killos
Assistant Examiner—Taylor Victor Oh

(57) ABSTRACT

A compound shown by the following formula:

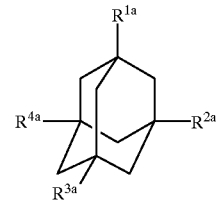

wherein each of $R^{1a}$, $R^{2a}$, $R^{3a}$ and $R^{4a}$ represents a substituent selected from a non-reactive atom, a non-reactive group, a hydroxyl group and an amino group, and at least two members selected from $R^{1a}$, $R^{2a}$, $R^{3a}$ and $R^{4a}$ are a hydroxyl group, a carboxyl group or an amino group; is subjected to an esterification reaction or an amidation reaction with a polymerizable unsaturated compound (e.g., an alcohol, a carboxylic acid, an amine) in the presence of a catalyst comprising an element selected from the Group 3 elements, such as a samarium compound, to obtain a polymerizable adamantane derivative having at least one polymerizable unsaturated group in high yield.

14 Claims, No Drawings

POLYMERIZABLE ADAMANTANE DERIVATIVES AND PROCESS FOR PRODUCING THE SAME

This application is the national phase under 35 U.S.C. §371 of prior PCT International Application No. PCT/JP98/02085 which has an International filing date of May 12, 1998 which designated the United States of America.

DESCRIPTION

1. Technical Field

The present invention relates to a process for producing a polymerizable adamantane derivative useful for providing a functional polymer, a catalyst useful for synthesizing polymerizable adamantane derivatives, and the novel polymerizable adamantane derivative.

2. Background Art

Photo-curable polymers or monomers have been utilized in various fields, for example, as photosensitive resins and covering agents for optical fibers, besides paint compositions, paints, coating agents such as printing inks and adhesives. Among such photo-setting polymers or monomers, polycyclic hydrocarbons [e.g., norbornene (meth)acrylate, adamantane (meth)acrylate] are useful for producing coating layers or moldings which are excellent in optical properties, mechanical properties and the like.

Japanese Patent Application Laid-open No. 33350/1988 (JP-A-63-33350) [Japanese Patent Publication No. 61980/1995 (JP-B-7-61980)] proposes to produce adamantane mono(meth)acrylate by bromating an adamantane, hydrolyzing to introduce a hydroxyl group thereto, then esterifying it by using a (meth)acrylic acid or (meth) acrylic acid halide. In the introduction of a hydroxyl group, however, it is required that an adamantane is bromated by using a large amount (e.g., 10 mole or more) of bromine, and that a formed bromide is hydrolyzed with an expensive reagent containing silver (e.g., silver nitrate or silver sulfate) in a stoichiometric excess amount [Chem. Ber., 92 1629(1959), 93 226,1161(1960): J. Org. Chem., 26 2207(1961)]. Moreover, in this method, reacting at a temperature of about 100° C. for hours is required. Specifically, in this method, it is difficult to considerably improve production efficiencies of an adamantane mono(meth)acrylate and yields. Further, in this method, a halogen remains, which is unfavorable in view of safe hygiene and environmental hygiene.

In the above-mentioned esterification, use of (meth) acrylic acid halide (in particular chloride) is advantageous, relative to (meth)acrylic acid, to enhance yields of the objective compounds. In a process using acid halides such as a (meth)acrylic acid chloride, however, separation of amine hydrochloride is required because amines, as a dehydrogen halide agent, are used together with the halides. However, the separation of the amine hydrochloride is considerably difficult, in addition, the separation of excess amines by distillation or recrystallization deteriorates yields of the objective compounds.

As a process for providing an adamantandiol, Japanese Patent Publication No. 16621/1967 (JP-B-42-16621) discloses that adamantanediol is obtained by allowing adamantane to react, in a concentrated acetic acid solution, by using 5-fold mole or more of chromic acid relative to adamantane. In this process, adamantandiol can be formed, however, a treatment of chromium components is required. In addition, oxidation of adamantane does not proceed to the level of polyol bodies such as tri- or more alcohol bodies even under severer reaction conditions.

A preferred oxidation process, from the viewpoints of resources and the environment, is a catalytic oxidation process, which is conducted with the direct use of molecular oxygen or air as an oxidizing agent. In page 762 of the "Lecture Draft II" (1994) of 67th Spring Annual Meeting of Chemical Society of Japan and Japanese Patent Application Laid-open No. 38909/1996 (JP-A-8-38909), it is disclosed that adamantane is oxidized with oxygen by using an oxidation catalyst comprising an imide compound (e.g., N-hydroxyphthalimide) to produce adamantanemonool.

It is conceivable that adamantane mono(meth)acrylate or poly(meth)acrylate is formed by subjecting the adamantanemonool or adamantanepolyol produced in such manner to esterification reaction with (meth)acrylic acid or acid halide. However, since the esterification reaction is an equilibrium reaction, and an esterification efficiency of an alcohol body of adamantane (especially, an adamantanepolyol having plural hydroxyl groups) is low, it is difficult to obtain adamantane (meth)acrylate (in particular, an adamantane poly(meth)acrylate having plural (meth)acryloyl groups) in a high yield.

In the Lecture Draft II (pages 1178 and 1179) of 69th Spring Annual Meeting of Chemical Society of Japan, it is reported that equilibratory advantageous amidation reaction of an ester compound having a simple structure proceeds more efficiently, in the presence of samarium catalyst, than in the presence of a conventional Lewis acid catalyst.

It is, therefore, an object of the present invention to provide a process which can inhibit admixture of an halogen component and produce an adamantane derivative having at least one polymerizable unsaturated group in a high yield.

It is another object of the present invention to provide a process for producing a polymerizable adamantane derivative wherein a highly pure adamantane derivative having at least one polymerizable unsaturated group may effectively be formed with high efficiency, and a catalyst for synthesizing the polymerizable adamantane derivative.

A further object of the present invention is to provide a process for producing a polymerizable adamantane derivative wherein a polymerizable unsaturated group may effectively be introduced to the adamantane derivative by esterification or amidation in a mild or moderate condition, and a catalyst for synthesizing the polymerizable adamantane derivative.

It is still another object of the present invention to provide a novel polymerizable adamantane derivative useful for providing a functional polymer and the like.

A still further object of the present invention is to provide a polymerizable adamantane derivative which does not have a halogen component substantially.

DISCLOSURE OF INVENTION

The inventors of the present invention did intensive research, and finally found that (a) oxidation of adamantane with oxygen, in the presence of an oxidation catalyst comprising an imide compound (e.g., N-hydroxyphthalimide) and a specific transition metal compound, provides not only adamantanemonool but also an adamantanepolyol in high efficiency, and (b) a highly pure adamantane derivative having at least one polymerizable unsaturated bond is formed by conducting an esterification or amidation of the formed adamantanemonool or adamantanepolyol with a polymerizable unsaturated compound, in the presence of a catalyst comprising a rare earth metal compound. The present invention has been accomplished based on the above findings.

Thus, in the present invention, a compound shown by the following formula (1a) (adamantane derivative):

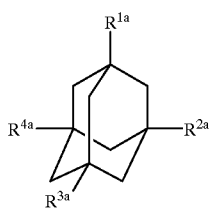

(1a)

wherein $R^{1a}$, $R^{2a}$, $R^{3a}$ and $R^{4a}$ independently represent at least one substituent selected from a non-reactive atom, a non-reactive group, a hydroxyl group, a hydroxymethyl group, a carboxyl group, an amino group and a reactive group derived therefrom, and at least one of $R^{1a}$, $R^{2a}$, $R^{3a}$ and $R^{4a}$ is a hydroxyl group, a hydroxymethyl group a carboxyl group, an amino group or a reactive group derived therefrom, is subjected to esterification reaction or amidation reaction, in the presence of a catalyst comprising a compound containing a Group 3A element of the Periodic Table of Elements, with at least one compound (polymerizable unsaturated compound (1b)) selected from an alcohol having a polymerizable unsaturated bond, a carboxylic acid, an amine and a reactive derivative thereof to provide a polymerizable adamantane derivative shown by the following formula (1):

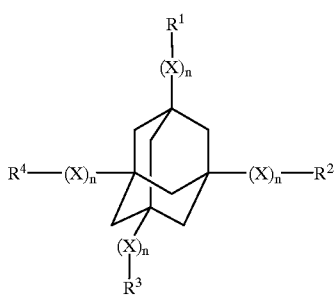

(1)

wherein $R^1$, $R^2$, $R^3$ and $R^4$ independently represent at least one substituent selected from a non-reactive atom, a non-reactive group and a polymerizable unsaturated group, and at least one of $R^1$, $R^2$, $R^3$ and $R^4$ is a polymerizable unsaturated group; X represents a connecting group comprising an ester bond or an amide bond, n denotes 0 or 1, and X may be different from each other according to $R^1$, $R^2$, $R^3$ and $R^4$, with the proviso that n is 0 when $R^1$, $R^2$, $R^3$ or $R^4$ is a non-reactive atom and a non-reactive group.

In the polymerizable adamantane derivative, the polymerizable unsaturated group usually has a polymerizable unsaturated double bond, for example, an α,β-ethylenically unsaturated double bond such as vinyl group, isopropenyl group and allyl group.

Further, the present invention comprises a catalyst for producing a polymerizable adamantane derivative having at least one polymerizable unsaturated group, namely, a catalyst for producing the polymerizable adamantane derivative represented by the formula (1) by reacting the adamantane derivative (1a) with the polymerizable unsaturated compound (1b), and this catalyst comprises a compound containing a Group 3A element of the Periodic Table of Elements.

An adamantane derivative of the present invention is shown by the following formula (3):

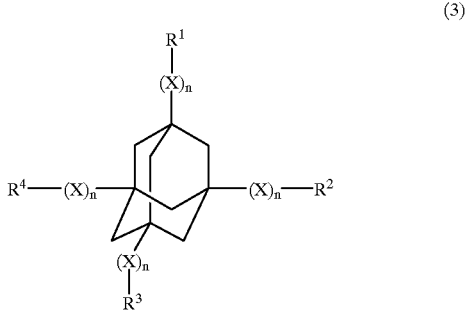

(3)

wherein $R^1$, $R^2$, $R^3$ and $R^4$ may be the same or different and may each represent at least one substituent selected from a non-reactive atom, a non- reactive group and a polymerizable unsaturated group, and at least one of $R^1$, $R^2$, $R^3$ and $R^4$ is a polymerizable unsaturated group; X denotes a —OC(=O)—group in which the left end thereof is intended to be a moiety bound to an adamantane back bone; n denotes 0 or 1 with the proviso that n denote 0 when $R^1$, $R^2$, $R^3$ or $R^4$ is a non-reactive atom or a non-reactive group; and when the number of the polymerizable unsaturated group is one or two, at least one member selected from $R^1$, $R^2$, $R^3$ and $R^4$ is a non-reactive group selected from the group consisting of nitro group, amino group which may be protected by a protective group or an N-substituted amino group which may be protected by a protective group, carboxyl group which may be protected by a protective group and hydroxymethyl group which may be protected by a protective group.

Moreover, the present invention also comprises a polymerizable adamantane derivative which is shown by the formula (1) or (3) and the amount of halogen remaining is about 70 ppm or less.

In the present specification, the term "esterification" means esterification in a wide sense such as various reactions forming an ester bond, for instance, a direct reaction of an carboxylic acid with an alcohol, a reaction of a reactive derivative of a carboxylic acid (e.g., a carboxylic acid ester, a carboxylic acid halide, a carboxylic acid anhydride) with an alcohol, and a reaction of a carboxylic acid salt with an alkyl halide. The term "protective group" or "protecting group" is used in a wide sense and comprises a group derived from a free functional group, and it may be impossible to eliminate the protective or protecting group.

BEST MODE FOR CARRYING OUT THE INVENTION

In the adamantane derivative shown by the formulae (1a), (1) and (3), a methylene moiety of the adamantane back bone (e.g., 2-, 4-, 6- or 8-position) may be substituted with various substituents, such as an oxo group, a halogen atom (e.g., bromine, chlorine, fluorine), a $C_{1-4}$ alkyl group (e.g., methyl group, ethyl group).

The adamantane derivative shown by the formula (1a) comprises an adamantanemonool or adamantanepolyol, adamantanemonocarboxylic acid or adamantanepolycarboxylic acid, adamantanemonoamine or adamantanepolyamine, or reactive derivatives thereof, each corresponding to the polymerizable adamantane derivative (1).

As to $R^{1a}$, $R^{2a}$, $R^{3a}$ and $R^{4a}$ of the adamantane derivative (1a) (or $R^1$, $R^2$, $R^3$ and $R^4$ of the polymerizable adamantane (1)), a non-reactive atom and non-reactive group is a substituent inert to esterification or amidation, and may be the same or different according to $R^{1a}$ to $R^{4a}$ (or $R^1$ to $R^4$). Examples of a non-reactive atom and non-reactive group include at least one substituent selected from the group consisting of hydrogen atom, a halogen atom, an alkyl group, hydroxyl group, carboxyl group, nitro group, amino group, an N-substituted amino group, nitrile group, hydroxymethyl group and the like.

And the "non-reactive atom" or "non-reactive group" may be selected depending upon the embodiment of the esterification or amidation, provided that it is inert to esterification or amidation reaction. For example, in a reaction of an adamantane having a hydroxyl group and a carboxyl group with a carboxyl group-containing polymerizable unsaturated compound or derivative thereof such as (meth)acrylic acid, a carboxyl group in the an adamantane is a non-reactive group. In the reaction of the adamantane with a hydroxyl group-containing polymerizable unsaturated compound such as 2-hydroxyethyl(meth)acrylate, a hydroxyl group in the adamantane is a non-reactive group. Further, in an adamantane having an alkoxycarbonyl group, when reacted with a hydroxyl group- or an amino group-containing polymerizable compound, for example, a $C_{1-6}$alkoxy-carbonyl group (especially, a $C_{1-4}$alkoxy-carbonyl group) belongs to reactive groups in certain conditions (conditions of transesterification reaction or amidation reaction).

The halogen atoms comprise fluorine, chlorine, bromine and iodine. Alkyl groups include, for instance, $C_{1-6}$alkyl group such as methyl, ethyl, propyl, isopropyl, butyl, isobutyl, s-butyl, t-butyl, especially $C_{1-4}$alkyl groups (among them, $C_{1-2}$alkyl groups).

As alkoxy groups, there may be exemplified, a $C_{1-6}$alkoxy group such as methoxy, ethoxy, propoxy, isopropoxy, butoxy, isobutoxy, s-butoxy, t-butoxy, specifically, a $C_{1-4}$alkoxy group.

Alkoxycarbonyl groups include, for example, a $C_{1-6}$alkoxy-carbonyl group such as methokycarbonyl, ethoxycarbonyl, propoxycarbonyl, isopropoxycarbonyl, butoxycarbonyl, isobutoxycarbonyl, s-butoxycarbonyl, t-butoxycarbonyl, particularly a $C_{1-4}$alkoxy-carbonyl group.

Acyloxy groups include, for instance, an aliphatic $C_{2-6}$acyloxy group such as acetyloxy, propionyloxy, isopropionyloxy, butylyloxy, isobutylyloxy, valeryloxy, isovaleryloxy, pivaloyloxy, preferably an aliphatic $C_{2-4}$acyloxy group.

An amino group as the non-reactive group or reactive group may be an N-substituted amino group. Examples of the N-substituted amino group include a mono- or di$C_{1-6}$alkylamino group such as methylamino, ethylamino, propylamino, dimethylamino, diethylamino, preferably a mono- or di$C_{1-4}$alkylamino group.

A hydroxyl group, a hydroxymethyl group, a carboxyl group or an amino group as the non-reactive group or reactive group may be protected by a protective group. Examples of a group protected by a protective group include the above-mentioned alkoxy group, alkoxycarbonyl group.

As a protective group of a hydroxyl group and a hydroxymethyl group, there may be exemplified the above-mentioned alkyl groups (i.e., $C_{1-6}$alkyl groups, preferably $C_{1-4}$alkyl groups), cycloalkyl groups (e.g., cyclohexyl group), aryl groups (e.g., 2,4-dinitrophenyl group), aralkyl groups (e.g., benzyl group, 2,6-dichlorobenzyl group, 2-nitrobenzyl group, a benzyl group which may have a substituent such as triphenylmethyl group), tetrahydropyranyl group, non-polymerizable acyl groups [e.g., an aliphatic acyl groups such as acetyl, propionyl, isopropionyl, butylyl, isovaleryl, preferably aliphatic $C_{2-6}$acyl groups, especially aliphatic $C_{2-4}$acyl groups, aromatic acyl groups such as benzoyl group (especially aromatic $C_{7-13}$acyl groups), alicyclic acyl groups such as cyclohexyl carbonyl group], the above-mentioned alkoxy-carbonyl groups (e.g., $C_{1-6}$alkoxycarbonyl groups), aralkyloxycarbonyl groups (e.g., benzyloxycarbonyl group), carbamoyl groups which may have a substituent such as a $C_{1-6}$alkyl group, a $C_{6-14}$aryl group (e.g., carbamoyl, methylcarbamoyl, ethylcarbamoyl, phenylcarbamoyl groups), di$C_{1-4}$alkylphosphynothioyl groups, diarylphosphynothioyl groups. Preferred protective groups of hydroxyl group and hydroxymethyl group include alkyl groups, non-polymerizable acyl groups (in particular, aliphatic acyl groups), alkoxycarbonyl groups, carbamoyl groups which may have a substituent and the like.

A protective group for amino group comprises those exemplified in the item of the protective group for hydroxyl group, for example, t-butyl group, an aralkyl group, a non-polymerizable acyl group, an alkoxycarbonyl group, an aralkyloxycarbonyl group, a dialkylphosphinothioyl group, a diarylphosphinothioyl group. A preferred protective group for amino group comprises, for example, a saturated $C_{2-6}$aliphatic acyl group (particularly a saturated $C_{2-4}$aliphatic acyl group), a $C_{7-13}$aromatic acyl group, a $C_{1-6}$alkoxy-carbonyl group.

A protective group for carboxyl group includes, for example, the above exemplified alkoxy group (e.g., a $C_{1-6}$alkoxy group, especially a $C_{1-4}$alkoxy group), a cycloalkyloxy group (e.g., cyclohexyloxy group), an aryloxy group (e.g., phenoxy group), an aralkyloxy group (e.g., benzyloxy group), a tri$C_{1-4}$alkylsllyloxy group, an amino group which may have a substituent [e.g., amino group; an N-substituted amino group such as mono- or di$C_{1-6}$alkylamino group (e.g., methylamino group, dimethylamino group, ethylamino group, diethylamino group)], hydrazino group, an alkoxycarbonylhydrazino group (e.g., t-butoxycarbonylhydrazino group), an aralkyloxycarbonyl-hydrozino group (e.g., benzyloxycarbonylhydrazyno group). As a preferred protective group for carboxyl group, there may be exemplified an alkoxy group, an amino group which may have a substituent.

In the adamantane derivative (1a), at least one member selected from $R^{1a}$, $R^{2a}$, $R^{3a}$ and $R^4$ is at least one group selected from hydroxyl group, hydroxymethyl group, carboxyl group, amino group, and a reactive group derived from them, and such groups function as reactive groups in esterification reaction or amidation reaction. In $R^{1a}$, $R^{2a}$, $R^{3a}$ and $R^{4a}$, species of the reactive groups may be the same or different from each other. In a preferred embodiment, the adamantane derivative (1a) usually has about 1 to 4 hydroxyl groups or carboxyl groups (especially hydroxyl groups) relative to 1 molecule.

In the adamantane derivative (1a), the substitution site (or moiety) of the reactive group is not strictly limited, but may be a methylene moiety, and usually a methine carbon moiety of adamantane (i.e., 1-, 3-, 5- or 7-position).

In the polymerizable unsaturated compound (1b), the polymerizable unsaturated group comprises, for example, a hydrocarbon group having a polymerizable double bond (e.g., an allyl-$C_{1-4}$alkyl group such as vinyl group, isopropenyl group, an allyl group, an allylmethyl group; an α-alkyl group-substituted vinyl-$C_{1-4}$alkyl group such as 1-propenyl group, 2-butenyl group) and a hydrocarbon group having a polymerizable triple bond (e.g., ethynyl-$C_{1-4}$alkyl group such as ethynyl group, 2-propynyl group). A preferred polymerizable unsaturated group has an α,β-ethylenycally unsaturated bond (e.g., vinyl group, isopropenyl group, an allyl group, especially vinyl group or isopropenyl group). Such polymerizable unsaturated groups may be the same or different from each other according to $R^{1a}$, $R^{2a}$, $R^{3a}$ and $R^{4a}$.

As an alcohol having a polymerizable unsaturated bond among the polymerizable unsaturated compounds as (1b), there may be exemplified, a compound having an unsaturated double bond [e.g., an allyl alcohol; a hydroxyalkyl (meth)acrylate (e.g., a hydroxy$C_{2-6}$alkyl (meth)acrylate such as 2-hydroxyethyl (meth)acrylate, 2-hydroxypropyl (meth) acrylate, 3-hydroxypropyl (meth)acrylate, 4-hydroxybutyl (meth)acrylate, 6-hydroxyhexyl (meth)acrylate); a (poly) oxy$C_{2-4}$alkylene glycol mono(meth)acrylate such as a diethylene glycol mono(meth)acrylate, a triethylene glycol mono (meth)acrylate, a polyethylene glycol mono(meth)acrylate, a dipropylene glycol mono(meth)acrylate, a tripropylene glycol mono(meth)acrylate, a polypropylene glycol mono (meth)acrylate, a polyoxytetramethyleneglycol mono(meth) acrylate], a compound having an unsaturated triple bond [e.g., propalgyl alcohol]. As a reactive derivative of such alcohols, there may be exemplified, an allyl halide (e.g., an allyl chloride, an allyl bromide).

As examples of a carboxylic acid having a polymerizable unsaturated bond, there may be exemplified compounds having an unsaturated double bond [e.g. monocarboxylic acids such as (meth)acrylic acid, crotonic acid, vinylacetic acid and allylacetic acid; polycarboxylic acids such as maleic acid, fumaric acid and itaconic acid; and monoalkylester of the polycarboxylic acid], and compounds having an unsaturated triple bond [e.g. propiolic acid].

The reactive derivatives of such carboxylic acids include acid anhydrides [e.g. (meth)acrylic anhydride, maleic anhydride], compounds having a leaving group (e.g. a halogen atom, an alkyl group, an alkenyl group, an alkynyl group, an aryl group, a cycloalkyl group, an aralkyl group).

The reactive derivatives of carboxylic acids having a leaving group include, for example, acid halides [e.g. (meth) acrylic chloride, (meth)acrylic bromide], carboxylic acid alkyl esters [e.g. carboxylic acid $C_{1-6}$alkyl esters (particularly, carboxylic acid lower $C_{1-4}$alkyl esters) such as methyl (meth)acrylate, ethyl (meth)acrylate, propyl (meth)acrylate, butyl (meth)acrylate, isobutyl (meth) acrylate and t-butyl (meth)acrylate], carboxylic acid alkenylesters [e.g. carboxylic acid $C_{2-6}$alkenyl esters (particularly, carboxylic acid $C_{2-6}$alkenyl esters, among them, specifically, carboxylic acid $C_{2-4}$alkenyl esters) such as vinyl (meth) acrylate, allyl (meth)acrylate, 1-propenyl (meth)acrylate, isopropenyl (meth)acrylate, 1-butenyl (meth)acrylate, 2-butenyl (meth)acrylate, 3-butenyl (meth)acrylate and 2-pentenyl (meth)acrylate], carboxylic acid alkynyl esters [e.g. carboxylic acid $C_{2-10}$alkynyl esters (particularly, carboxylic acid $C_{2-6}$alkynyl esters, among them, specifically carboxylic acid $C_{2-4}$alkynyl esters) such as ethynyl (meth) acrylate and propynyl (meth)acrylate], carboxylic acid aryl esters [e.g. phenyl (meth)acrylate], carboxylic acid cycloalkyl esters [e.g. carboxylic acid $C_{3-10}$cycloalkyl esters such as cyclohexyl (meth)acrylate], carboxylic acid aralkyl esters [e.g. carboxylic acid phenyl-$C_{1-4}$alkyl esters such as benzyl (meth)acrylate].

Examples of a preferred reactive derivative include carboxylic acid halides, carboxylic acid lower $C_{1-6}$alkyl esters (particularly, $C_{1-4}$alkylesters), carboxylic acid $C_{2-6}$alkenyl esters (particularly, $C_{2-4}$alkenyl esters) and carboxylic acid $C_{2-6}$alkynyl esters (particularly, $C_{2-4}$alkynyl esters). Particularly, when a carboxylic acid halide or a carboxylic acid $C_{2-6}$alkenyl ester is used, a corresponding polymerizable adamantane derivative can be produced with high selectivity and yield by the exchange reaction of a leaving group while inhibiting a side reaction such as an addition polymerization.

As examples of an amine having a polymerizable unsaturated bond, there may be exemplified compounds having an unsaturated double bond, such as allylamine, butenylamine and diallylamine.

Examples of a preferred compound having a polymerizable unsaturated bond include carboxylic acids having a polymerizable unsaturated bond and reactive derivatives thereof, particularly, carboxylic acids having an α,β-ethylenically unsaturated double bond or triple bond, or reactive derivatives thereof [e.g. carboxylic halides, carboxylic acid lower $C_{1-4}$alkyl esters, carboxylic acid $C_{2-4}$alkenyl esters]. As an organic carboxylic acid, an organic carboxylic acid having an α,β-ethylenically unsaturated double bond (particularly, acrylic acid, methacrylic acid, and the like) is advantageous.

Incidentally, in the method of the present invention, the production of an amine hydrochloride and the like can be inhibited, and when a carboxylic acid lower $C_{1-4}$alkyl ester or a carboxylic acid $C_{2-4}$alkenyl ester is used, contamination of the intended compound can be prevented by a halogen component. Moreover, since a compound having a low boiling point (e.g. the ester described above) can be used as a polymerizable unsaturated compound (1b)(a reactive component), a treatment after a reaction can be conducted without difficulty, and an isolation yield can be vastly improved.

In the present invention, an esterification reation (including an exchange reaction of a leaving group such as transesterification reaction) or an amidation reaction of the adamantane derivative (1a) with the polymerizable unsaturated compound (1b) is carried out in the presence of a catalyst composed of a compound comprising a Group 3 element of the Periodic Table of Elements in order to enhance reactivity to obtain the polymerizable adamantane derivative with high yield.

Referring to the catalyst of the present invention composed of a compound comprising a Group 3A element of the Periodic Table of Elements, as a Group 3A element of the Periodic Table of Elements, there may be exemplified rare earth elements [e.g. scandium, yttrium, lanthanoid-series elements (lanthanum, cerium, praseodymium, neodymium, promethium, samarium, europium, gadolinium, terbium, dysprosium, holmium, erbium, thulium, ytterbium, lutetium), actinoid series elements (e.g. actinium).

Examples of a preferred Group 3A element of the Periodic Table of Elements include rare earth elements such as scandium, yttrium and lanthanoid-series elements (e.g. samarium, gadolinium, ytterbium). Especially, samarium has a high catalytic activity.

Referring to the compound comprising a Group 3A element of the Periodic Table of Elements, the valence of a Group 3A element of the Periodic Table of Elements is not particularly restricted, and may be about 2 to 4 valence, practically divalent or trivalent. The above-mentioned compound comprising a Group 3A element of the Periodic Table of Elements is not restricted provided that has a catalytic activity, and may be a compound or a complex with a metal simple substance, an inorganic compound (e.g. a halide, an oxide, a double oxide, phosphorus compounds, a nitrogen compound) or an organic compound (e.g. an organic acid). A hydroxide containing the above element, an oxygen acid salt, an organic acid salt, an inorganic acid salt, a halide, a coordination compound (complex) each containing the above metal element are practically used. The complex may be a π-complex such as a metallocene compound. Further, the Group 3 element-containing compound may be a composite metal compound containing a different metal. These catalysts can be used either singly or in combination of two or more.

Hereinafter, taking a samarium compound for example, a component of a catalyst will be described concretely and, needless to say, a compound containing other Group 3A element of the Periodic Table of Elements corresponding to the samarium compound also can be used effectively.

The hydroxide includes, for example, a samarium (II) hydroxide, a samarium (III) hydroxide. The metal oxide includes, for example, a samarium (II) oxide, a samarium (III) oxide.

As the organic acid salt, there may be exemplified salts of organic acids such as organic carboxylic acids (e.g. monocarboxylic acids such as formic acid, acetic acid, trichloroacetic acid, trifluoroacetic acid, propionic acid, butyric acid, valeric acid, naphthenic acid and stearic acid; polycarboxylic acids such as oxalic acid and maleic acid), oxycarboxylic acids (e.g. glycolic acid, lactic acid, malic acid, tartaric acid, citric acid), thiocyanic acids and sulfonic acids (e.g. alkylsulfonic acids such as methanesulfonic acid, trichloromethanesulfonic acid, trifluoromethanesulfonic acid and ethanesulfonic acid; aryl sulfonic acids such as benzenesulfonic acid and p-toluenesulfonic acid). As the inorganic acid salt, there may be exemplified nitrates, sulfates, phosphates, carbonates and perchlorates. Concrete examples of the organic acid salt or inorganic acid salt are a samarium (II) acetate, a samarium (III) acetate, a samarium (II) trichloroacetate, a samarium (III) trichloroacetate, a samarium (II) trifluoroacetate, a samarium (III) trifluoroacetate, a samarium (II) trifluoromethanesulfate (i.e., samarium (II) triflate), a samarium (III) trifluoromethanesulfonic acid (i.e., samarium (III) triflate), a samarium (II) nitrate, a samarium (II) sulfate, a samarium (II) phosphate and a samarium (II) carbonate.

The halide includes a fluoride, a chloride, a bromide and an iodide, and there may be exemplified a samarium (II) iodide, a samarium (III) iodide, a samarium (II) bromide, a samarium (III) bromide, a samarium (II) chloride, a samarium (III) chloride.

A ligand constituting a complex includes, for example, OH (hydroxo), an alkoxy group such as methoxy, ethoxy, propoxy and butoxy group; an acyl group such as acetyl and propionyl group; an alkoxycarbonyl group such as methoxycarbonyl (acetato) and ethoxycarbonyl group; an acetylacetonato, a cyclopentadienyl, $C_{1-4}$alkyl-substituted cyclopentadienyls (e.g. $C_{1-2}$alkyl-substituted cyclopentadienyls such as pentamethylcyclopentadienyl), dicyclopentadienyl, $C_{1-4}$alkyl-substituted dicyclopentadienyls (e.g. $C_{1-2}$alkyl-substituted dicyclopentadienyls such as pentamethyldicyclopentadienyl); halogen atoms such as chlorine and bromine; CO; CN; oxygen atom; $H_2O$ (aquo); phosphorus compounds such as phosphines (e.g. triarylphosphines such as triphenylphosphine); nitrogen-containing compounds such as $NH_3$ (ammine), NO, $NO_2$ (nitro), $NO_3$ (nitrato), ethylenediamine, diethylenetriamine, pyridine, phenanthroline. In the complexes or complex salts, the same or different ligand may be coordinated singly or in combination.

Among the above complexes, as the samallocene-type complex, there may be exemplified a diacetylacetonatosamarium (II), a triacetylacetonatosamarium (III), a dicyclopentadienylsamarium (II), a tricyclopentadienylsamarium (III), a dipentamethylcyclopentadienylsamarium (II), a tripentamethylcyclopentadienylsamarium (III).

When the Group 3A element-containing compound [e.g. a divalent samallocene-type complex having a high-electron-donative pentamethylcyclopentadienyl ligand [e.g. $(C_5Me_5)_2Sm$; (PMSM)], a halogen compound of samarium, or an alkoxide or a hydroxide compound of samarium] is used as a catalyst, not only in an amidation reaction, but also in an esterification reaction in spite of an equilibrium reaction, the esterifaction proceeds with a higher reaction efficiency than that of a Lewis acid catalyst or a protonic acid catalyst while inhibiting side reactions. The catalyst of the present invention is advantageous for the production of the above polymerizable adamantane derivative (1) employing an exchange reaction of a leaving group such as transesterification reaction.

The catalyst composed of the compound comprising a Group 3A element may be whichever of a homogeneous system or a heterogeneous system. Moreover, the catalyst may be a solid catalyst in which a catalytic component supported on a support or carrier, and the catalytic component is constituted of a Group 3A element-containing compound. As the support or carrier, porous supports such as active carbon, zeolite, silica, silica-almina, bentonite are practically used. In the solid catalyst, a supported amount of the catalyst component is about 0.1 to 50 parts by weight of the Group 3A element-containing compound, preferably about 0.5 to 30 parts by weight and more preferably about 0.1 to 20 parts by weight, relative to 100 parts by weight of the support.

The amount of the catalyst composed of the above Group 3A element-containing compound may be selected within a wide range. To give an example, the amount can be selected from the ranges of about 0.1 mole % to 1 equivalent, preferably 0.5 to 50 mole %, more preferably 1 to 25 mole % (e.g. 5 to 20 mole %), relative to the above adamantane derivative (1a).

The aforementioned esterification or amidation reaction is advantageous when conducted in the presence of an oxime. The oxime may be whichever of an aldoxime or ketoxime. Examples of the oxime are aliphatic oximes such as 2-hexanone oxime, alicyclic oximes such as cyclo-hexanone oxime, aromatic oximes such as acetophenone oxime, benzophenone oxime and benzyl dioxime.

The amount of the oxime can be selected within a wide range of, for example, about 0.1 mole % to 1 equivalent, preferably 1 to 50 mole % and more preferably 5 to 40 mole % (e.g. 5 to 30 mole %), relative to the adamantane derivative (1a).

The ratio of the polymerizable unsaturated compound (1b) to the adamantane derivative (1a) is not specifically restricted so far as not adversely affecting the production efficiency of the polymerizable adamantane derivative (1). The amount of the polymerizable unsaturated compound (1b) may be about 0.5 to 5 mole, preferably about 0.8 or more (e.g. about 0.8 to 5mole) and particularly about 1 mole or more (e.g. about 1 to 3 mole, particularly about 1 to 1.5 mole), relative to 1 equivalent of the adamantane derivative (1a) (i.e., the weight of the adamantane derivative per hydroxyl group, carboxyl group, amino group, or reactive derivative group thereof). Since the esterification reaction is an equilibrium reaction, a larger amount of the polymerizable unsaturated compound (1b) makes the reaction more advantageous in its process. However, since the catalyst of the present invention has a very high catalytic activity, an excessive amount of the polymerizable unsaturated compound (1b) is unnecessary. In particular, in the reaction of a combination which is disadvantageous from the point of view of reaction equilibrium, when the above alkenyl ester (e.g. vinyl ester) having a vinylic leaving group is used as the polymerizable unsaturated compound (1b), even if the compound (1b) in an amount of about 1 mole or less (e.g. about 0.4 to 1 mole, preferably about 0.5 to 1 mole) per 1 equivalent of the leaving group of the adamantane derivative (1a) is used, the reaction immediately goes to completion, and good results are obtained.

In contrast to the high reaction heat produced by the conventional method employing an acid halide such as (meth)acrylic chloride, according to the method of the present invention, the reaction heat is low. Therefore, even with the solvent in a small amount, the reaction proceeds smoothly and the objective compound can be produced in high yield.

The above esterification reaction or amidation reaction may be carried out either in the presence or absence of a solvent inert to the reaction. Examples of such reactive solvent are aliphatic hydrocarbons such as hexane, octane; alicyclic hydrocarbons such as cyclohexane; aromatic hydrocarbons such as benzene, toluene and xylene; ketones such as acetone, methyl ethyl ketone and methylisobutyl ketone; ethers such as dioxane, diethyl ether and diisopropyl ether, tetrahydrofuran; non-polar protic solvents such as dimethylformamide, dimethylacetamide, N-methylpyrolidone, acetonitrile and benzonitrile; and mixed solvents thereof. As the reactive solvent, the polymerizable unsaturated compound (1b) also may be used.

Among adamantane derivatives (1a), a compound having a plurality of, for example, hydroxyl groups or carboxyl groups has high hydrophilicity, and the reaction system tends to be heterogeneous when the prevailing reactive solvent for esterification (e.g. hydrophobic solvents such as toluene) is used. Therefore, when the adamantane derivative having high hydrophilicity is used, as the preferred solvent, there may be exemplified hydrophilic solvents (e.g. ketones such as acetone and methyl ethyl ketone; ethers such as dioxane, diethyl ether and tetrahydrofuran; non-polar protic solvents) and a mixed solvent of a hydrophilic solvent and a hydrophobic solvent (e.g. an aliphatic, or an alicyclic or an aromatic hydrocarbon.)

Since the above reaction is an equilibrium reaction, the reaction is advantageously accelerated when a reaction inhibitive component such as a leaving component is immediately removed from the reaction system. The leaving component is advantageously removed when a solvent having a high boiling point (e.g. an organic solvent having a boiling point of about 50 to 120° C., particularly 60 to 115° C.) or an azeotropic solvent (e.g. the above hydrocarbons) are used.

The temperature for an esterification or an amidation reaction may be selected within a range of, for example, about 0 to 150° C., preferably about 25 to 120° C. When the catalyst composed of the above Group 3 element-containing compound is used, even under mild or moderate conditions, the polymerizable adamantane derivative can be produced with high efficiency. In this case, the reaction temperature may be, for example, 0 to 150° C., preferably 10 to 100° C. and more preferably 20 to 80° C. In particular, the reaction can smoothly be conducted, even under mild conditions of about 20 to 50° C., by using, for example, the above organic carboxylic acid alkenyl ester as the above polymerizable unsaturated compound (1b). The reaction can be conducted under ambient pressure or reduced pressure, or under pressure (under a load). Moreover, the reaction can be effected in a conventional manner such as in a batch system, semi-batch system or continuous system.

Such reaction makes it possible to produce the polymerizable adamantane derivative represented by the aforementioned formula (1) with high efficiency.

In the polymerizable adamantane derivative (1), X is a connecting group for connecting an adamantane to a polymerizable unsaturated group, and composed of an ester bond (—COO—, —OCO—), or an amide bond (—NHCO—, —CONH—). The connecting group may be a group having an ester bond (e.g. —CH$_2$COO—), or a group having an amide bond. Generally, X is composed of an ester bond.

Typical examples of the connecting group X having the above polymerizable unsaturated group are (meth)acryloyloxy group, (meth)acryloyloxymethyl group, (meth)acryloylamino group, (meth)acryloyloxy-C$_{2-10}$alkyloxycarbonyl group, allyloxy carbonyl group, allylamino carbonyl group.

In the aforementioned formula (1), n stands for 0 or 1, X may be different according to $R^1$, $R^2$, $R^3$ and $R^4$. Moreover, if whichever of $R^1$, $R^2$, $R^3$ and $R^4$ is a non-reactive atom such as a hydrogen atom or a non-reactive group, n denotes 0.

Typical examples of the compounds represented by the aforementioned formula (1) are polymerizable adamantane derivatives having an ester bond [(meth)acrylates, e.g., 1,3-bis[(meth)acryloyloxy] adamantane, 1,7-bis[(meth)acryloyloxy] adamantane, 1,3,5-tris[(meth)acryloyloxy] adamantane, 1,3,7-tris[(meth)acryloyloxy] adamantane, 1,3,5,7-tetrakis[(meth)acryloyloxy] adamantane; adamantanes having a (meth)acryloyloxy-C$_{2-10}$alkyloxy group, such as 1,3-bis[(2-(meth)acryloyloxyethyl)oxycarbonyl] adamantane, 1,7-bis[(2-(meth)acryloyloxyethyl) oxycarbonyl] adamantane, 1,3,5-tris[(2-(meth)acryloyloxyethyl)oxycarbonyl] adamantane, 1,3,7-tris[(2-(meth)acryloyloxyethyl)oxycarbonyl] adamantane and 1,3,5,7-tetrakis[(2-(meth)acryloyloxyehtyl)oxycarbonyl] adamantane; allyl esters, e.g., 1,3-bis(allyloxycarbonyl) adamantane, 1,7-bis(allyloxycarbonyl) adamantane, 1,3,5-tris(allyloxycarbonyl) adamantane, 1,3,7-tris (allyloxycarbonyl) adamantane, 1,3,5,7-tetrakis (allyloxycarbonyl) adamantane]; polymerizable adamantane derivatives having an amide bond [(meth)acrylamides, e.g., 1,3-bis[(meth)acryloylamino] adamantane, 1,7-bis[(meth)acryloylamino] adamantane, 1,3,5-tris[(meth)acryloylamino] adamantane, 1,3,7-tris[(meth)acryloylamino] adamantane, 1,3,5,7-tetrakis[(meth)acryloylamino] adamantane; allyl amides, e.g., 1,3-bis (allylaminocarbonyl) adamantane, 1,7-bis (allylaminocarbonyl) adamantane, 1,3,5-tris (allylaminocarbonyl) adamantane, 1,3,7-tris (allylaminocarbonyl) adamantane, 1,3,5,7-tetrakis (allylaminocarbonyl) adamantane]. These compounds may have at least one substituent selected from various substitutents, e.g., a halogen atom, an alkyl group, a hydroxyl group which may be protected by a protective group (e.g. hydroxyl group, an alkoxy group, an acyloxy group, carbamoyloxy group), a carboxyl group which may be protected by a protective group (e.g. carboxyl group, an alkoxycarbonyl group, a carbamoyl group which may have a substituent), an amino group which may be protected by a protective group (e.g. amino group, an acyl amino group, an alkoxycarbonyl amino group), an N-substituted amino group, a nitro group, a hydroxymethyl group which may be protected by a protective group. The substituent may be substituted at a suitable position in an adamantane (particularly, whichever of the 1,3,5 and 7- positions in the adamantane skeleton).

These polymerizable adamantane derivatives (1), by a conventional method, can be easily separated and purified after completion of the reaction. Examples of the conventional methods are, for example, separation methods such as filtration, concentration, distillation, extraction, crystallization, recrystallization and column chromatography, and combination methods thereof.

[Method for producing an adamantane derivative (1a)]

The adamantane derivative (1a), as a raw material of the polymerizable adamantane derivative, may be prepared by introducing at least one reactive group selected from the group consisting of a hydroxyl group, a hydroxymethyl group, a carboxyl group, an amino group and a reactive derivative group thereof to an adamantane in which $R^{1a}$, $R^{2a}$, $R^{3a}$ and $R^{4a}$ have at least one substituent selected from a non-reactive atom or a non-reactive group (hereinafter, referred to simply as an adamantane). The number of the above substituent of the adamantane is usually about 0 to 3 per 1 molecule, and the species of the substituents may be different from each other according to the species of the adamantane derivative (1a). Further, if necessary, adamantanes of which the reactive group has a substitution rate lower than that of the objective compound (1a) can also be used.

As the adamantane (substrate), there may be exemplified an adamantane, a halogen-containing adamantane (particularly, a chlorine-, or bromine-substituted adamantane), an alkyl group-containing adamantane (particularly, a $C_{1-2}$alkyl group-substituted adamantane), a hydroxyl group-containing adamantane which may be protected by a protective group [e.g. a hydroxyl group-containing adamantane, an alkoxy group-containing adamantane (particularly, a $C_{1-2}$alkoxy group-substituted adamantane), an acyloxy group-containing adamantane, an alkoxycarbonyloxy group-containing adamantane, a carbamoyloxy group-containing adamantane which may have a substituent], a carboxyl group-containing adamantane which may be protected by a protective group [a carboxyl group-containing adamantane, an alkoxycarbonyl group-containing adamantane (e.g. a $C_{1-4}$alkoxycarbonyl group-containing adamantane), a carbamoyl group-containing adamantane which may have a substituent], a nitro group-containing adamantane, an amino group-containing adamantane which may be protected by a protective group (e.g. an amino group-containing adamantane, an alkoxycarbonylamino group-containing adamantane, an acylamino group-containing adamantane), an N-substituted amino group-containing adamantane (e.g. a $C_{1-6}$acylamino group-containing adamantane, a mono-, or di-$C_{1-4}$alkylamino group-containing adamantane), a hydroxymethyl group-containing adamantane which may be protected by a protective group.

An adamantane may have a plurality of different species of substituents. For example, 1-methyl-3-adamantanol, 1-methyl-3-carboxyadamantane, 1-methyl-3-nitroadamantane, 1-carboxy-3-adamantanol, 1-nitro-3-adamantanol, 1-nitro-3-carboxyadamantane may also be used.

As an adamantane, a compound that is commercially available can also be employed. Further, a reactive group or a substituent may be introduced to adamantanes by the following method.

[Hydroxyl group-containing adamantane derivative]

Among the adamantane derivatives represented by the aforementioned formula (1a), the compounds having a hydroxyl group can be obtained by a conventional oxidation method, e.g., oxidation method employing a nitric acid or a chromic acid, oxygen-oxidation method employing a cobalt salt as a catalyst, biochemical oxidation method. The hydroxyl group-containing adamantane derivatives can also be obtained by introducing a halogen atom (e.g. bromine atom), then hydrolyzing with the use of inorganic salts such as silver nitrate, silver sulfate, whereby introducing a hydroxyl group. In a preferred method, the hydroxyl group-containing adamantane derivative can be obtained by oxidizing the substrate corresponding to the aforementioned formula (1a) with oxygen in the presence of an oxydatiqn catalyst composed of an imide compound represented by the following formula (2) or of an catalyst composed of the above imide compound (2) and a co-catalyst.

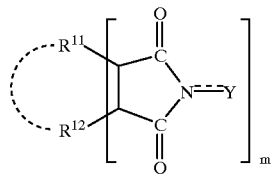

(2)

(In the formula, $R^{11}$ and $R^{12}$ independently represent a hydrogen atom, a halogen atom, an alkyl group, an aryl group, a cycloalkyl group, a hydroxyl group, an alkoxy group, a carboxyl group, alkoxylcarbonyl group, or an acyl group, or $R^{11}$ and $R^{12}$ may bond together to form a double bond or an aromatic and non-aromatic ring; Y represents an oxygen atom or a hydroxyl group, and the bond between the nitrogen atom "N" and "Y" is a single bond or a double bond. m denotes an integer of 1 to 3.

[Imide compound (2)]

In the compound shown by the formula (2), a halogen atom, as the substituents $R^{11}$ and $R^{12}$, includes an iodine, a bromine, a chlorine and a fluorine atom. The alkyl group includes a straight chain or branched chain $C_{1-10}$alkyl group such as methyl, ethyl, propyl, isopropyl, butyl, isobutyl, s-butyl, t-butyl, pentyl, hexyl, heptyl, octyl and decyl. An illustrative preferred alkyl group includes a lower $C_{1-6}$alkyl group, in particular a lower $C_{1-4}$alkyl group. As the aryl group, there may be mentioned, for instance, a phenyl group and a naphthyl group. Examples of the cycloalkyl group include cyclopentyl, cyclohexyl, and cyclooctyl group. The alkoxy group includes, for example, $C_{1-10}$alkoxy groups such as methoxy, ethoxy, propoxy, isopropoxy, butoxy, isobutoxy, t-butoxy, pentyloxy and hexyloxy. Among them, lower $C_{1-6}$alkoxy group, particularly a lower $C_{1-4}$alkoxy group is preferable.

Examples of the alkoxycarbonyl group include $C_{1-10}$alkoxy-carbonyl groups such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl. A preferred alkoxycarbonyl group includes lower $C_{1-6}$alkoxy-carbonyl groups, particularly lower $C_{1-4}$alkoxycarbonyl groups.

The acyl group includes, for instance, $C_{1-6}$acyl groups such as formyl, acetyl, propionyl, butyryl, isobutyryl, valeryl, isovaleryl and pivaloyl group.

The substituents $R^{11}$ and $R^{12}$ may be the same or different from each other. In the formula (1), $R^{11}$ and $R^{12}$ may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, and it may practically be a hydrocarbon ring. As such a ring, there may be mentioned, for instance, non-aromatic alicyclic rings (e.g., cycloalkane rings which may have a substituent such as a cyclohexane ring, optionally substituted cycloalkene rings such as a cyclohexene ring), non-aromatic bridged (cross-linked) rings (e.g., optionally substituted bridged hydrocarbon rings such as a 5-norbornene ring), optionally substituted aromatic rings such as a benzene ring and a naphthalene ring. The ring may practically comprise an aromatic ring.

A preferred imide compound (2) includes compounds shown by the following formulae.

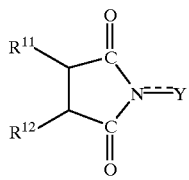
(2a)

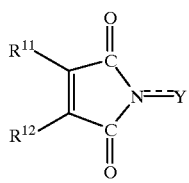
(2b)

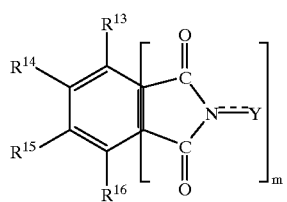
(2c)

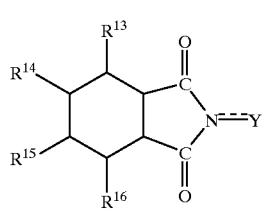
(2d)

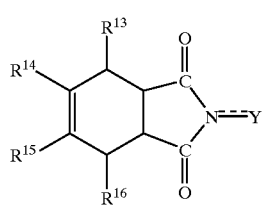
(2e)

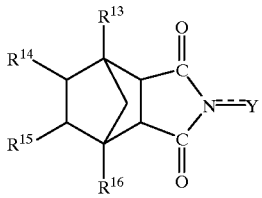
(2f)

(In the formula, $R^{13}$ to $R^{16}$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; $R^{11}$, $R^{12}$ and m have the same meanings as defined above.)

In the substituents $R^{13}$ to $R^{16}$, the alkyl group includes alkyl groups similar to those exemplified above, in particular $C_{1-6}$alkyl groups. The alkoxy group includes the same alkoxy groups as mentioned above, in particular lower $C_{1-4}$alkoxy groups. Examples of the alkoxycarbonyl group include the same alkoxycarbonyl groups as exemplified above, particularly lower $C_{1-4}$alkoxycarbonyl groups. As the acyl group, there may be mentioned acyl groups similar to those mentioned above, in particular $C_{1-6}$acyl groups. Examples of the halogen atom include fluorine, chlorine and bromine atoms. The substituents $R^{13}$ to $R^{16}$ may practically be a hydrogen atom, a lower $C_{1-4}$alkyl group, a carboxyl group, a nitro group or a halogen atom, respectively.

The symbol X in the formula (2) denotes an oxygen atom or a hydroxyl group. A bond between the nitrogen atom "N" and "Y" is a single bond or a double bond. Further, m usually denotes about 1 to 3, preferably 1 or 2. The imide compound shown by the formula (2) may be used singly or in combination in the oxidation reaction.

As examples of the acid anhydride corresponding to the imide compound of the formula (2), there may be mentioned saturated or unsaturated aliphatic dicarboxylic acid anhydrides such as succinic anhydride, maleic anhydride, saturated or unsaturated nonaromatic cyclic polycarboxylic acid anhydrides (alicyclic polycarboxylic anhydrides) such as tetrahydrophthalic anhydride, hexahydrophthalic anhydride (1,2-cyclohexanedicarboxylic anhydride), 1,2,3,4-cyclohexanetetracarboxylic acid 1,2-anhydride, bridged cyclic polycarboxylic anhydrides (alicyclic polycarboxylic anhydrides) such as hetic anhydride, himic anhydride, aromatic polycarboxylic anhydrides such as phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride.

Examples of a preferred imide compound include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide and so forth. A typically preferable compound includes an N-hydroxyimide compound derived from an alicyclic polycarboxylic anhydride, in particular from an aromatic polycarboxylic anhydride, such as N-hydroxyphthalimide.

The imide compound may be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

These imide compounds have high oxidation activity, and can catalystically accelerate the oxidation reaction of an admantane even under mild or moderate conditions. Further, when various species of substrates are oxidized in the coexistence of the imide compound and the co-catalyst, the conversion and/or selectivity coefficient of the hydroxyl group-containing derivative is improved.

[Co-catalyst]

A co-oxidizing agent as the co-catalyst includes or comprises a metal compound such as a compound comprising or containing a Group 2A element of the Periodic Table of Elements (e.g., magnesium, calcium, strontium, barium), a transition metal compound, and a compound containing a Group 3B element (e.g., boron B, aluminium Al) of the Periodic Table of Elements (e.g., a boron compound). These co-catalysts may be employed independently or in combination.

As the elements of the transition metal, there may be mentioned, for instance, Group 3A elements of the Periodic Table of Elements (e.g., scandium Sc, yttrium Y, and lanthanoid elements such as lanthanum La, cerium Ce, samarium Sm, actinoid elements such as actinium Ac), Group 4A elements of the Periodic Table of Elements (e.g., titanium Ti, zirconium Zr, hafnium Hf), Group 5A elements (e.g., vanadium V, niobium Nb, tantalum Ta), Group 6A elements (e.g., chromium Cr, molybdenum Mo, tungsten W), Group 7A elements (e.g., manganese Mn, technetium Tc, rhenium Re), Group 8 elements (e.g., iron Fe, ruthenium Ru, osmium Os, cobalt Co, rhodium Rh, iridium Ir, nickel Ni, palladium Pd, platinum Pt), Group 1B elements (e.g., copper Cu, silver Ag, gold Au) and Group 2B elements of the Periodic Table of Elements (e.g., zinc Zn, cadmium Cd).

A preferred element constituting the co-catalyst includes elements of the transition metals (e.g., Group 3A elements of the Periodic Table of Elements such as lanthanoid elements, actinoid elements, Group 4A elements, Group 5A elements, Group 6A elements, Group 7A elements, Group 8 elements, Group 1B elements, and Group 2B elements of the Periodic Table of Elements) and Group 3B elements of the Periodic Table of Elements (e.g., boron compounds). In particular, high oxidizing activities are demonstrated when the imide compound of the formula (2) is used in combination with a compound containing Group 4A elements such as Ti and Zr; Group 5A elements such as V; Group 6A elements such as Cr, Mo and W; Group 7A elements such as Mn, Tc and Re; Group 8 elements such as Fe, Ru, Co, Rh and Ni; or Group 1B elements such as Cu.

The species of the co-catalyst is not particularly limited as far as it contains the element and has oxidizing property, and it may be a simple substance or hydroxide of a metal. The co-catalyst may practically be an oxide of a metal (a double oxide or an oxygen acid salt) comprising the element, an organic acid salt, an inorganic acid salt, a halide, a coordinate compound (a complex) comprising the metal element, or a polyacid (a heteropolyacid, particularly an isopolyacid) or its salt.

As the boron compound, there may be mentioned, for example, a boron hydride (e.g., borane, diborane, tetraborane, pentaborane, decaborane), a boric acid (e.g., orthoboric acid, metaboric acid, tetraboric acid), a borate (e.g., a nickel borate, magnesium borate, manganese borate), boron oxides such as $B_2O_3$; nitrogen-containing boron compounds such as borazane, borazene, borazine, boron amide, boron imide; $BF_3$; $BCl_3$; halides such as tetrafluoroborate; esters of boric acid (e.g., methyl borate, phenyl borate).

The hydroxide includes $Mn(OH)_2$, $MnO(OH)$, $Fe(OH)_2$ and $Fe(OH)_3$, typically speaking. Examples of the metal oxide include $Sm_2O_3$, $TiO_2$, $ZrO_2$, $V_2O_3$, $V_2O_5$, $CrO$, $Cr_2O_3$ $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$, and so forth. As examples of the double oxide or oxygen acid salt, there may be mentioned $MnAl_2O_4$, $MnTiO_3$, $LaMnO_3$, $K_2Mn_2O_5$, $CaO.xMnO_2$ (x=0.5, 1, 2, 3, 5), manganate [e.g., manganates(V) such as $Na_3MnO_4$, $Ba_3[MnO_4]_2$; manganates(VI) such as $K_2MnO_4$, $Na_2MnO_4$, $BaMnO_4$; permanganates such as $KMnO_4$, $NaMnO_4$, $LiMnO_4$, $NH_4MnO_4$, $CsMnO_4$, $AgMnO_4$, $Ca(MnO_4)_2$, $Zn(MnO_4)_2$, $Ba(MnO_4)_2$, $Mg(MnO_4)_2$, $Cd(MnO_4)_2$].

As the organic acid salts, there may be exemplified salts with a $C_{2-20}$ fatty acid such as cobalt acetate, manganese acetate, cobalt propionate, manganese propionate, cobalt naphthenate, manganese naphthenate, cobalt stearate, manganese stearate, manganese thiocyanate, and corresponding salts of Ce, Ti, Zr, V, Cr, Mo, Fe, Ru, Ni, Pd, Cu and Zn. The inorganic acid salt includes, for instance, nitrates such as cobalt nitrate, iron nitrate, manganese nitrate, nickel nitrate, copper nitrate, and sulfates, phosphates and carbonates each corresponding to these nitrates (e.g., cobalt sulfate, iron sulfate, manganese sulfate, cobalt phosphate, iron phosphate, manganese phosphate, an iron carbonate, a manganese carbonate, iron perchlorate). As the halides, there may be mentioned halides, for instance, chlorides such as $SmCl_3$, $SmI_2$, $TiCl_2$, $ZrCl_2$, $ZrOCl_2$, $VCl_3$, $VOCl_2$, $MnCl_2$, $MnCl_3$, $FeCl_2$, $FeCl_3$, $RuCl_3$, $CoCl_2$, $RhCl_2$, $RhCl_3$, $NiCl_2$, $PdCl_2$, $PtCl_2$, $CuCl$, $CuCl_2$, or fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2$, $CuBr$, $CuBr_2$) and complex halides such as $M^1MnCl_3$, $M^1_2MnCl_4$, $M^1_2MnCl_5$, $M^1_2MnCl_6$, wherein $M^1$ represents a monovalent metal.

The ligand constituting the complex includes, for example, OH (hydroxo), alkoxy groups such as methoxy, ethoxy, propoxy, butoxy; acyl groups such as acetyl, propionyl; alkoxycarbonyl groups such as methoxycarbonyl (acetato), ethoxycarbonyl; acetylacetonato; cyclopentadienyl group; halogen atoms such as chlorine, bromine; CO; CN; oxygen atom; $H_2O$ (aquo), phosphorus compounds such as phosphine (e.g., triarylphosphine such as triphenylphosphine); nitrogen-containing compounds such as $NH_3$ (ammine), NO, $NO_2$ (nitro), $NO_3$ (nitrato), ethylenediamine, diethylenetriamine, pyridine, phenanthroline. In the complexes or complex salts, the same or different ligands may be coordinated singly or in combination.

The transition metal element and the ligand may optionally be employed in combination to form a complex. Such a complex includes, for instance, acetylacetonato complexes [e.g., acetylacetonato complex of Ce, Sm, Ti, Zr, V, Cr, Mo, Mn, Fe, Ru, Co, Ni, Cu or Zn, titanylacetylacetonato complex $TiO(AA)_2$, zirconylacetylacetonato complex $ZrO(AA)_2$, vanadylacetylacetonato complex $VO(AA)_2$], cyano complexes [e.g., hexacyanomanganate(I), hexacyanoferrate(II)], carbonyl complexes or cyclopentadienyl complexes [e.g., tricarbonylcyclopentadienylmanganese(I), biscyclopentadienylmanganese(II), biscyclopentadienyliron (II), $Fe(CO)_5$, $Fe_2(CO)_9$, $Fe_3(CO)_{12}$], nitrosyl compounds [e.g., $Fe(NO)_4$, $Fe(CO)_2(NO)_2$], thiocyanato complexes [e.g., thiocyanatocobalt, thiocyanatomanganese, thiocyanatoiron], or acetyl complexes [e.g. cobalt acetate, manganese acetate, iron acetate, copper acetate, zirconyl acetate $ZrO(OAc)_2$, titanyl acetate $TiO(OAc)_2$, vanadyl acetate $VO(OAc)_2$].

The polyacid (isopolyacid or heteropolyacid) is practically at least one member selected from Group 5A elements and Group 6A elements of the Periodic Table of Elements, such as V (vanadic acid), Mo (molybdic acid) and W (tungstic acid), typically speaking. There is no particular limit as to the central atom, and it may be any of, for instance, Cu, Be, B, Al, Si, Ge, Sn, Ti, Th, N, P, As, Sb, V, Nb, Ta, Cr, Mo, W, S, Se, Te, Mn, I, Fe, Co, Ni, Rh, Os, Ir, Pt, or Cu. As illustrative examples of the heteropolyacid, there may be mentioned cobaltmolybdate, cobalttungstate, molybdenumtungstate, manganesemolybdate, manganesetungstate, manganesemolybdenumtungstate, vanadomolybdophosphate, manganesevanadiummolybdate, and manganesevanadomolybdophosphate.

These co-catalysts may be employed independently or in combination depending on the species of a substrate and so forth.

As to the transition metal compound constituting of the co-catalysts, the valency of the element is not particularly restricted, and it may be about 2 to 6 valencies. The use of a divalent transition metal compound (e.g., a divalent cobalt compound, a divalent manganese compound) as the co-catalyst enhances oxidation activity. By way of illustration, a catalytic system comprising the imide compound in combination with a divalent transition metal compound instead of a trivalent transition metal compound may induce an oxidized product with high selectivity and in high yield within a short period of time.

Incidentally, the use of a compound containing at least one element selected from Group 4A elements (e.g., Ti, Zr), Group 6A elements (e.g., Cr. Mo) and Group 7A elements (e.g., Mn) of the Periodic Table of Elements as the co-catalyst considerably inhibits the inactivation (deactivation) of the catalyst (in particular the imide compound) even under severe reaction conditions. Therefore, the process insures oxidation of the substrate with oxygen or air with commercial advantages.

Further, the use of a compound containing a Group 4A element (e.g., Ti, Zr), Group 5A element (e.g., V), Group 6A element (e.g., Cr, Mo), Group 7A element (e.g., Mn) or Group 8 element (e.g., Fe, Co) of the Periodic Table of Elements as the co-catalyst results in remarkable enhancement of the oxidizing activity and provides effective oxidation of the substrate. By way of an example, a catalytic system comprising, as the co-catalyst, a compound containing a Group 5A element (e.g., V), Group 7A element (e.g., Mn) or Group 8 element (e.g., Co) of the Periodic Table of Elements has high activities. Specifically, the use of a compound containing a Group 5A element (e.g., V) as a co-catalyst insures or achieves an efficient oxidation of plural sites (in particular a methine carbon site) of a substrate and provides an adamantanepolyol to which plural hydroxyl groups are introduced. The oxidation catalyst comprising the imide compound (2), a compound containing a Group 7A element of the Periodic Table of Elements (e.g., a manganese compound), and a compound containing a Group 8 element of the Periodic Table of Elements (e.g., an iron compound) in combination has an improved and enhanced catalytic activities and provides an oxide effectively and advantageously with high conversion and selectivity. In such complex catalyst, the ratio of the compound containing a Group 8 element of the Periodic Table of Elements (the second co-catalyst) is not particularly limited, and practically, for instance, about 0.1 to 25 mole (e.g., about 0.1 to 20 mole), preferably about 0.2 to 15 mole, and more preferably about 0.5 to 10 mole relative to one mole of the compound containing the Group 7A element of the Periodic Table of Elements (the first co-catalyst).

Moreover, the use of the oxidation catalyst comprising the imide compound shown by the formula (2) and a co-catalyst containing a Group 1B element of the Periodic Table of Elements (e.g., Cu) considerably enhances selectivity in the oxidation reaction and inhibits the inactivation (deactivation) of the imide compound, hence commercially advantageous.

The oxidation catalyst comprising the imide compound or the oxidation catalytic system comprising the imide compound and the co-catalyst may be whichever of a homogeneous system or a heterogeneous system. The oxidation catalyst or the oxidation catalytic system may be a solid catalyst comprising a catalytic component supported on a support or carrier. As the support, use can be practically made of porous supports such as activated carbon, zeolite, silica, silica-alumina, bentonite. In the solid catalyst, the supported amount of the catalytic component may be about 0.1 to 50 parts by weight of the imide compound shown by the formula (2), preferably about 0.5 to 30 parts by weight and more preferably about 1 to 20 parts by weight relative to 100 parts by weight of the support. The ratio of the co-catalyst supported on the support is about 0.1 to 30 parts by weight, preferably about 0.5 to 25 parts by weight, and more preferably about 1 to 20 parts by weight, relative to 100 parts by weight of the support.

The relative ratio of the co-catalyst to the imide compound shown by the formula (2) may be selected from a range not interfering with the reaction velocity or rate and selectivity, and may be, for example, about 0.001 to 10 mole, preferably about 0.005 to 5 mole, more preferably about 0.01 to 3 mole and practically about 0.01 to 5 mole (in particular about 0.001 to 1 mole).

Incidentally, as the amount of the co-catalyst increase, the activity of the imide compound sometimes deteriorates. Therefore, for the purpose of maintaining high activity of the oxidation catalytic system, the proportion of the co-catalyst is not less than an effective amount to not more than about 0.1 mole (e.g., about 0.001 to 0.1 mole, preferably about 0.005 to 0.08 mole, and more preferably about 0.01 to 0.07 mole) relative to 1 mole of the imide compound.

The amount of the imide compound shown by the formula (2) in the oxidation reaction is selected from a broad range, and may for example be about 0.001 to 1 mole (0.01 to 100 mole %), preferably about 0.001 to 0.5 mole (0.1 to 50 mole %), more preferably about 0.01 to 0.30 mole and practically about 0.01 to 0.25 mole, relative to 1 mole of the substrate, typically speaking.

The amount of the co-catalyst (a co-oxidizing agent) can be suitably selected from a range not interfering with the reactivity and selectivity, and is, for example, about 0.0001 mole (0.01 mole %) to 0.7 mole (70 mole %), preferably about 0.0001 to 0.5 mole, more preferably about 0.001 to 0.3 mole, and practically about 0.0005 to 0.1 mole (e.g., 0.005 to 0.1 mole) relative to one mole of the substrate.

When a polyacid (an isopolyacid or a heteropolyacid) or salt thereof is used as a co-catalyst, the amount is 0.1 to 25 parts by weight, preferably 0.5 to 10 parts by weight, and more preferably 1 to 5 parts by weight relative to 100 parts by weight of the substrate.

In the oxidation reaction of adamantanes, the oxygen used in the oxidation may be active oxygen, but molecular oxygen is practically employed for economical advantages. Such molecular oxygen is not specifically limited, and use may be made of whichever of pure oxygen, or oxygen diluted with an inert gas such as nitrogen, helium, argon or carbon dioxide. From the viewpoints of not only handling and safety but also economy, air is preferably employed.

The amount of oxygen may be selected according to the species of an adamantane, from the range of about 0.5 mole or more (e.g., 1 mole or more), preferably about 1 to 100 mole, and more preferably about 2 to 50 mole relative to 1 mole of the substrate. The oxygen is practically used in an excess mole relative to an adamantane. In specific, the reaction is advantageously carried out in an atmosphere containing molecular oxygen such as air or oxygen gas.

The oxidation process of the present invention is usually conducted in an organic solvent inert to the reaction. As the organic solvents, there may be mentioned, for example, organic carboxylic acids (e.g., formic acid, acetic acid, propionic acid) or hydroxycarboxylic acids; nitriles such as acetonitrile, propionitrile, benzonitrile; amides such as formamide, acetamide, dimethylformamide (DMF), dimethylacetamide; alcohols such as t-butanol, t-amyl alcohol; aliphatic hydrocarbons such as hexane, octane; aromatic hydrocarbons such as benzene; halogenated hydrocarbons such as chloroform, dichloromethane, dichloroethane, carbon tetrachloride, chlorobenzene; nitro compounds such as nitrobenzene, nitromethane, nitroethane; esters such as ethyl acetate, butyl acetate; ethers such as dimethyl ether, diethyl ether, diisopropyl ether, dioxane; and mixtures of these solvents. Use may practically be made of, as the solvent, organic acids such as acetic acid, nitriles such as acetonitrile, benzonitrile.

When the reaction is carried out in the presence of a protonic acid, the oxidation reaction may be smoothly carried out and a desired compound is obtained with high selectivity and in a high yield. As mentioned above, the protonic acid may be used as a solvent.

As the protonic acid, there may be exemplified organic acids (e.g., organic carboxylic acids such as formic acid, acetic acid, propionic acid; hydroxycarboxylic acids such as oxalic acid, citric acid, tartaric acid; alkylsulfonic acids such as methanesulfonic acid, ethanesulfonic acid; arylsulfonic acids such as benzenesulfonic acid, p-toluenesulfonic acid), and inorganic acids (e.g., hydrochloric acid, sulfuric acid, nitric acid, phosphoric acid).

The oxidation process using the oxidation catalyst or the oxidation catalytic system is characterized in that the oxidation reaction smoothly proceeds even under comparatively mild or moderate conditions. The reaction temperature may be suitably selected according to the species of the catalytic system. The temperature is, for instance, about 0 to 300° C., preferably about 30 to 250° C., more preferably about 50 to 200° C., and practically about 70 to 150° C. In the production of an adamantanepolyol, the reaction at a temperature of about 40 to 150° C., in particular about 60 to 120° C. (e.g., about 70 to 110° C.) tend to provide an adamantanepolyol within a short period of time.

The reaction may be carried out under ambient pressure (atmospheric pressure) or under pressure (under a load). When the reaction is conducted under pressure, the pressure is, usually, about 1 to 100 atm (e.g., about 1.5 to 80 atm), preferably about 2 to 70 atm, and more preferably about 5 to 50 atm. The reaction time may be suitably chosen within a range of about 30 minutes to 48 hours, preferably about 1 to 36 hours, and more preferably about 2 to 24 hours, according to the reaction temperature and pressure.

[A carboxyl group-containing adamantane derivative]

As a process for introducing a carboxyl group to an adamantane, various processes are available. In order to produce a carboxyl group efficiently, it is advantageous to employ a carboxylation process which comprises, as in the oxidation reaction, contacting an adamantane with carbon monoxide and oxygen in the presence of a catalyst comprising the imide compound (2) or a catalytic system comprising the imide compound (2) and a co-catalyst.

Carbon monoxide or oxygen used in the carboxylation reaction may be pure or diluted with an inert gas. Air may be used as an oxygen source.

In the carboxylation reaction, the amount of the imide compound shown by the formula (2), the amount of the co-catalyst, and the ratio of the imide compound (2) to the co-catalyst may be selected within each range mentioned in the paragraphs of the oxidation reaction.

The amount of the carbon monoxide is selected within the range of 1 mole or more (e.g., about 1 to 1000 mole), preferably excess mole, for example 1.5 to 100 mole, (e.g., about 2 to 50 mole), and more preferably about 2 to 30 mole (e.g., about 5 to 25 mole) relative to 1 mole of a substrate.

The amount of oxygen is selected within the range of 0.5 mole or more (e.g., about 0.5 to 100 mole), preferably about 0.5 to 30 mole, and more preferably about 0.5 to 25 mole relative to 1 mole of a substrate.

The ratio of the carbon monoxide (CO) to oxygen ($O_2$) may be selected within the broad range as far as being within the above mentioned range, for example $CO/O_2$=about 1/99 to 99.99/0.01 (mole %). It is advantageous to employ carbon monoxide in an amount larger than that of oxygen. The ratio of CO to $O_2$ may be selected within the range of about $CO/O_2$=1/99 to 99/1 (mole %) [e.g., about 10/90 to 99/1 (mole %)], and is preferably about 30/70 to 98/2 (mole %), more preferably about 50/50 to 95/5 (mole %), and practically about 60/40 to 90/10 (mole %).

The volume ratio of carbon monoxide to oxygen in the supply line may be selected within the range of, for example, $CO/O_2$=about 1/99 to 99.99/0.01 (volume %), and is, for example, usually about 1/99 to 99/1 (volume %), preferably about 30/70 to 98/2 (volume %), more preferably about 50/50 to 95/5 (volume %), and practically about 60/40 to 90/10 (volume %).

The carboxylation reaction may be carried out in an organic solvent inert to the reaction. As the organic solvent, the organic solvent exemplified for the oxidation reaction, such as an organic acid (e.g., carboxylic acids such as acetic acid), a nitrile (e.g., acetonitrile) and a hydrocarbon halide (e.g., dichloroethane), may be used.

The carboxylation reaction using the imide compound (2) proceed smoothly even under comparatively mild or moderate conditions. The reaction temperature may be selected within the range of, for example, about 0 to 200° C., preferably about 10 to 150° C. (e.g., about 10 to 120° C.), and more preferably about 10 to 100° C. (e.g., about 10 to 80° C.) according to the species of the imide compound or the substrate. The reaction may be carried out under ambient pressure (atmospheric pressure) or under pressure (under a load).

[A hydroxymethyl group-containing adamantane]

A hydroxymethyl group-containing adamantane derivative may be produced by reducing the carboxyl group-containing adamantane derivative by a conventional process such as a catalytic hydrogenation using hydrogen or by a process using a hydrogenation reducing agent. A hydrogenation reducing agent includes, for example, sodium boron hydride-Lewis acid, aluminium hydride, lithium aluminium hydride, lithium trialkoxyaluminium hydride, and diborane.

[An adamantane having a nitro group or an amino group]

Introduction of a nitro group to an adamantane or an adamantane having a substituent may be carried out by a conventional process, for example, a process using a nitrating agent (e.g., a mixed acid of sulfuric acid and nitric acid, nitric acid, nitric acid and an organic acid (e.g., carboxylic acids such as acetic acid), a nitrate and sulfuric acid and dinitrogen pentaoxide). A preferred nitration process includes, for example, a nitration process which comprises contacting an adamantane with a nitrogen oxide in the presence or absent of the imide compound shown by the formula (2). The nitration reaction is advantageously carried out in the presence of a catalytic system (a catalytic system comprising the imide compound shown by the formula (2) and the co-catalyst) similar to that used in the above-mentioned oxidation reaction.

The nitrogen oxide may be respresented by the formula $N_xO_y$ (wherein x denotes an integer of 1 or 2 and y denotes an integer of 1 to 6).

In the compound shown by the above formula, when x is 1, y is usually an integer of 1 to 3; and when x is 2, y is usually an integer of 1 to 6.

Examples of such nitrogen oxide are $N_2O$, $NO$, $N_2O_3$, $NO_2$, $N_2O_4$, $N_2O_5$, $NO_3$ and $N_2O_6$. These nitrogen oxides may be used independently or in combination.

The preferred nitrogen oxide includes (i) a nitrogen oxide (particularly $N_2O_3$) generated by the reaction of at least one nitrogen oxide selected from dinitrogen oxide ($N_2O$) and nitrogen monoxide (NO) with oxygen, or a nitrogen oxide containing $N_2O_3$ as a main component and (ii) a nitrogen dioxide ($NO_2$) or a nitrogen oxide containing $NO_2$ as a main component.

Nitrogen oxide $N_2O_3$ may be easily obtained by a reaction of $N_2O$ and/or NO with oxygen. To be more concrete, it may be prepared by introducing nitrogen monoxide and oxygen to a reactor to produce a blue liquid $N_2O_3$. Therefore, the nitration reaction may be carried out by introducing $N_2O$ and/or NO and oxygen to a reaction system without previously producing $N_2O_3$ in advance.

Incidentally, oxygen may be pure or distilled with an inert gas (e.g., carbon dioxide, nitrogen, helium and argon). Air may be used as an oxygen source.

In other embodiment, among nitrogen oxides, when nitrogen dioxide ($NO_2$) is used, a nitration reaction smoothly proceeds even in the absence of oxygen. Therefore, a reaction system using $NO_2$ does not necessarily require oxygen. $NO_2$ may be used with oxygen.

The amount of the imide compound shown by the formula (2) may be selected within the range similar to that of the oxidation of an adamantane with oxygen.

The amount of the nitrogen oxide may be selected, according to the amount of nitro group to be introduced, within the range of, for example, about 1 to 50 mole, preferably about 1.5 to 30 mole and may practically be about 2 to 25 mole relative to 1 mole of an adamantane.

The nitration reaction is usually carried out in an organic solvent inert to the reaction. The organic solvent may be selected from the solvents similar to those exemplified in the paragraphs of the oxidation reaction. As a solvent, an organic acid (e.g., carboxylic acids such as acetic acid), a nitrile (e.g., acetonitrile and benzonitrile) and a hydrocarbon halide (e.g., dichroloethane) are practically used.

When employing the catalyst comprising the imide compound (2), the nitration reaction smoothly proceeds even under comparatively mild and moderate conditions. The reaction temperature is selected, according to the species of the imide compound or a substrate, within the range of, for example, about 0 to 150° C., preferably about 25 to 125° C., and more preferably about 30 to 100° C. The nitration reaction may be carried out under ambient pressure (atmospheric pressure) or under pressure (under a load).

An adamantane derivative having an amino group may be produced by subjecting a nitro group-containing adamantane derivative to a reduction reaction. The reduction reaction may be carried out by a conventional process such as a catalytic hydrogenation using hydrogen as a reducing agent and a reducing process using a hydrogenation reducing agent.

In the catalytic hydrogenation, for example, a metal simple substance(e.g., platinum, palladium, nickel, cobalt, iron and copper) and a compound comprising such metal element (e.g., platinum oxide, palladium black, palladium carbon and copper chromite) may be used as a catalyst. The amount of the catalyst is practically about 0.02 to 2 mole relative to 1 mole of an adamantane (substrate). In a catalytic hydrogenation, the reaction temperature may be, for example, about −20 to 100° C. (e.g., about 0 to 70° C.). A hydrogen pressure is practically about 1 to 10 atm.

In the reducing process using a hydrogenation reducing agent, the hydrogenation reducing agent includes, for example, aluminium hydride, sodium boron hydride and diborane. The amount of the hydrogenation reducing agent is usually 1 mole or more (e.g., about 1 to 10 mole) relative to 1 mole of a substrate. In the reducing process using the hydrogenation reducing agent, the reaction temperature is practically about 0 to 200° C. (e.g., about 0 to 170° C.).

The reduction reaction (the catalytic hydrogenation and the process using the hydrogenation reducing agent) may be carried out in the presence of a solvent (any solvent exemplified in the paragraphs of the oxidation reaction such as a carboxylic acid, an ether, an ester or an amide) inert to the reductive reaction.

A halogen-containing adamantane derivative may be produced by a conventional process, for example, by subjecting the hydroxyl group-containing adamantane to a reaction with a halogenating agent (e.g., hydrogen chloride; phosphrus halogenide such as phosphorus pentachloride, phosphorus trichloride; and thionyl chloride) or with chlorine or bromine. An alkoxy group-containing adamantane derivative may be obtained by reacting the hydroxyl group-containing adamantane with alkyl halide. An alkoxycarbonyl group-containing adamantane derivative may be obtained by reacting a carboxyl group-containing adamantane (or a reactive derivative thereof) with an alcohol. An amide group-containing adamantane derivative (e.g., a carbamoyl group-containing adamantane derivative which may have a substituent) may be obtained by reacting a carboxyl group-containing adamantane (or a reactive derivative thereof) with ammonia or an amine (a primary or secondary amine).

An acyloxy group-containing adamantane derivative and an acylamino group-containing adamantane derivative may be obtained, for example, by allowing a hydroxyl group-containing adamantane and an amino group-containing adamantane derivative to react with an acylating agent respectively. An alkoxycarbonyloxy group-containing adamantane derivative and an alkoxycarbonylamino group-containing adamantane derivative may be obtained, for example, by allowing a hydroxyl group-containing adamantane derivative and an amino group-containing adamantane derivative to react with a halocarbonate respectively. A carbamoyloxy group-containing adamantane derivative may be obtained, for example, by allowing a hydroxyl group-containing adamantane derivative to react with an isocyanate compound. An N-substituted amino group-containing adamantane derivative may be obtained, for example, by allowing the amino group-containing adamantane to react with a hydrocarbon halide (e.g., aliphatic hydrocarbon halide such as iodomethane, iodoethane, iodobutane, bromomethane, bromoethane, bromobutane, chloromethane, chloroethane). The reaction of the amino group-containing adamantane with the hydrocarbon halide may be carried out in the presence of a dehalogenating agent comprising an organic or inorganic basic compound.

Incidentally, before, after or during the oxidation reaction, a nitration reaction, a reductive reaction, or the esterification reaction, a hydroxyl group, an carboxyl group, an amido group or an amino group may be protected by a protecting group by a conventional process. The elimination of the protecting group may be carried out by a conventional process, for example, using an acid, an alkali, or ion-exchange resin.

Among the polymerizable adamantane derivatives (1) and adamantane derivatives (1a), a compound having a basic group or an acidic group may be in the form of a salt. A carboxyl group-containing adamantane derivative may form a salt by reacting with a basic compound (e.g., an organic base such as an organic amine; and an inorganic base such as ammonia and an alkali metal compound). An amino group-containing adamantane derivative may form a salt by reacting with an acid. The acid includes, for example, an inorganic acid (e.g., hydrochloric acid, sulfuric acid and nitric acid) and an organic acid (e.g., an aliphatic carboxylic acid such as acetic acid and propionic acid; an aromatic carboxylic acid such as benzoic acid; an alkylsulfonic acid such as methanesulfonic acid and ethanesulfonic acid; and an arylsulfonic acid such as benzenesulfonic acid and p-toluenesulfonic acid).

[A novel polymerizable adamantane derivative]

Among the compounds shown by the formula (1), the polymerizable adamantane derivative shown by the formula (3) is novel. The polymerizable adamantane derivative is useful as a raw material (a polymerizable monomer) of a functional polymer. In the formula (3), an atom or a group represented by $R^1$, $R^2$, $R^3$ or $R^4$ (e.g., a non-reactive atom, a non-reactive group, a polymerizable unsaturated group, an amino group or a N-substituted amino group) includes an atom or a group similar to that of the formula (1).

A typical compound of the polymerizable adamantane derivative includes, for example, a nitro group-containing polymerizable adamantane derivative such as 1-(meth)acryloyloxy-3-nitroadamantane, 1,3-bis[(meth)acryloyloxy]-5-nitroadamantane; a carboxyl group-containing polymerizable adamantane derivative such as 1-carboxy-3-(meth)acryloyloxyadamantane, 1-(meth)acryloyloxy-3-methoxycarbonyl adamantane, 1-carboxy-3,5-bis[(meth)acryloyloxy]adamantane and 1-(meth)acryloyloxy-3-(N,N-dimethylcarbamoyl)adamantane; a hydroxymethyl group-containing adamantane derivative such as 1-hydroxymethyl-3-(meth)acryloyloxyadamantane; an amino group or a N-substituted amino group-containing polymerizable adamantane derivative such as 1-acetylamino-3-(meth)acryloyloxyadamantane and 1-(meth)acryloyloxy-3-methoxycarbonylaminoadamantane; and a polymerizale adamantane derivative having not less than three polymerizable unsaturated groups such as 1,3,5-tris[(meth)acryloyloxy]adamantane. A substituent of these compounds may be protected by a protecting group.

A polymerizable adamantane derivative (3) may be obtained by a reaction similar to the above reaction (e.g., the oxidation reaction, the carboxylation reaction, the nitration reaction, the esterification reaction and the amidation reaction). In the production of the polymerizable adamantane derivative (3), the esterification reaction and/or the amidation reaction may be carried out by a conventional manner, for example, in the presence of an acid catalyst or an alkali catalyst, and advantageously in the presence of a catalyst comprising the compound containing a Group 3 element of the Periodic Table of Elements.

Incidentally, a reaction such as the oxidation reaction may be carried out in any of a batch system, semi-batch system or continuous system. After completion of the reaction, a reaction product can be easily isolated and purified according to a conventional technology, such as filtration, condensation, distillation, extraction, crystallization, recrystallization, column chromatography, or other isolation means, or a combination of these technologies.

A preferred polymerizable adamantane derivative and a polymer thereof include an adamantane derivative in which a residual amount by weight of a halogen is 70 ppm or less (e.g., about 0 to 60 ppm), preferably 50 ppm or less, more preferably 25 ppm or less (e.g., about 0 to 15 ppm) and particularly 10 ppm or less (e.g., 5 ppm or less). In a most preferred plymerizable adamantane derivative is one in which a halogen component is not detected substantially and the residual amount by weight of a halogen is 1 ppm or less. The species of halogen is not particularly restricted, and it may be fluorine or iodine, and is practically chlorine or bromine.

A polymer of the polymerizable adamantane derivative may be a homopolymer or a copolymer with a copolymerizable monomer.

These polymerizable adamantane derivatives may be obtained by allowing the adamantane derivative shown by the formula (1a) (e.g., a hydroxyl group-containing adamantane derivative) to react with at least one polymerizable compound (1b) (e.g., an organic carboxylic acid, an organic carboxylic acid alkyl ester and an organic carboxylic acid alkenyl ester having α,β-ethylentically unsaturated double bond or triple bond) selected from the group consisting of an alcohol, a carboxylic acid, an amine and a reactive derivative, containg no halogen atom thereof each having a polymerizable unsaturated bond in the presence of the compound containing a Group 3 elements of the Periodic Table of Elements.

Moreover, in order to reduce the residual amount of a halogen, it is preferable that an adamantane derivative induced with no reactive group, among the adamantane derivatives shown by the formula (1a) is subjected to at least one step selected from the following oxidation step (i), the carboxylation step (ii) and the nitration step (iii) to produce a compound introduced with at least one reactive group selected from the group consisting of a hydroxyl group, a carboxyl group and a nitro group, and the resultant compound is subjected to the esterification or amidation reaction:

(i) an oxidation step with oxygen in the presence of a catalyst comprising the imide compound shown by the formula (2);

(ii) a carboxylation step with carbon monoxide and oxygen in the presence of a catalyst comprising the imide compound shown by the formula (2); and (iii) at least one of a nitration step among the following (iiia), (iiib) and (iiic)

(iiia) a nitration step by a nitrogen oxide in the presence of a catalyst comprising the imide compound shown by the formula (2);

(iiib) a nitration step by at least one of a nitrogen oxide among a dinitrogen oxide and nitrogen monoxide with oxygen; and (iiic) a nitration step by nitrogen dioxide.

The adamantane derivative to which no reactive group is introduced includes an adamantane derivative of the formula (1a) wherein $R^{1a}$, $R^{2a}$, $R^{3a}$ and $R^{4a}$ are same or different from each other and represent a hydrogen atom, a non-reactive atom or a non-reactive group, and at least one member selected from $R^{1a}$, $R^{2a}$, $R^{3a}$, and $R^{4a}$ is a hydrogen atom.

Incidentally, at least one group selected from a hydroxymethyl group and an amino group may be produced by subjecting the reaction product obtained at the carboxylation step (ii) and/or the nitration step (iii) to a reduction step.

Such polymerizable adamantane derivative and polymer thereof (a homopolymer or a copolymer) contain a considerable little residual amount of a halogen, and are preferable at the point of safety sanitation and environment sanitation, and may inhibit coloring.

INDUSTRIAL APPLICABYLITY

A polymerizable adamantane derivative obtained by a process of the present invention can be thermal polymerizable and photopolymerizable in the presence or absent of a polymerization initiator (or a photopolymerization initiator). A polymer of the polymerizable adamantane derivative is superior in optical characters, machine characters, thermal characters and electrical characters. Therefore, the polymerizable adamantane derivative may be utilized for various purposes, for example, as a high-functional material (e.g., an optical material such as an optical fiber or covering agent thereof, an optical element, an optical lens, a hologram, an optical disk, and a contact lens, a coating agent for an organic glass, a conductive polymer, a photographic photosensitive material and a fluorescent material), a coating agent (including a paint), adhesives and a reforming agent of a polymer.

In the present invention, while inhibiting a halogen component from mixing, an adamantane derivative having a polymerizable unsaturated group can be obtained in high yield. A highly pure polymerizable adamantane derivative may be effectively obtained in high efficiency. In particular, while side reaction is inhibited, a polymerizable unsaturated group can be efficiently introduced to an adamantane derivative.

A polymerizable adamantane derivative of the present invention is useful for obtaining a functional polymer having superior characters.

The following example are intended to describe the present invention in more detail, but should by no means be construed to limit the scope of the invention. Inorganic acid ion, such as halogen compound ions and nitric acid ion were analyzed by liquid chromatography for anion detection.

EXAMPLES

Preparation Example 1

To 25 mmol of acetic acid were added 10 mmol of adamantane, 1 mmol of N-hydroxyphthalimide (NHPI) and a binary co-catalyst [0.03 mmol of acetylacetonatovanadium $V(AA)_3$ and 0.02 mmol of actylacetonatomangan $Mn(AA)_3$], and the resultant mixture was stirred in an oxygen atmosphere at a temperature of 75° C. for 6 hours. The products in the reaction mixture were analyzed by gas chromatography, and, as a result, the adamantane was converted into 1-adamantanol (yield: 37%). 1,3-adamantanediol (yield: 35%). 1,3,5-adamantanetriol (yield: 5%), 1,3,5,7-adamantane-tetranol (yield: 4%) with the adamantane conversion of 100%. The spectrum data of the 1,3,5,7-adamantanetetranol was as follows:

$^1$H-NMR(CDCl$_3$)δ: 1.602, 4.893

$^{13}$C-NMR(CDCl$_3$)δ: 52.3, 71.6

$IR(cm^{-1})$: 3306, 2947, 1455, 1332, 1210, 1046, 1004, 971, 559

Preparation Example 2

To 25 ml of acetic acid were added 10 mmol of adamantane, 2 mmol of NHPI and 0.1 mmol of acetylacetonatovanadium $V(AA)_3$, and the resultant mixture was stirred in an oxygen atmosphere at a temperature of 85° C. for 10 hours. The analysis of the product in the reaction mixture revealed that the adamantane was converted into 1-adamantanol (yield: 8%), 1,3-adamantanediol (yield: 22%), 1,3,5-adamanetriol (yield: 33%) and 1,3,5,7-adamantanetetraol (yield: 20%) with the adamantane conversion of 99%.

Preparation Example 3

To 25 ml of acetic acid were added 10 mmol of adamantane, 0.8 mmol of NHPI and 0.6 mmol of acetylacetonatocobalt(II)$Co(AA)_2$, and the resultant mixture was stirred in an oxygen atmosphere at a temperature of 75° C. for 3 hours. The products in the reaction mixture were analyzed by gas chromatography, and, as a result, adamantane was converted into 1-adamantanol (yield: 48%) and 1,3-adamantanediol(yield: 13%) with the adamantane conversion of 65%.

Comparative Example 1

To 2 ml of dioxane were added 0.168 g (1.00 mmol) of adamantanediol and 0.222 g (2.20 mmol) of triethylamine at a temperature of 50° C. To the resultant mixture was added dropwise in dioxane (2 ml) a solution of with 0.2 g (2.20 mmol) of acrylic acid chloride at a temperature of 50° C. for 1 hour, and then, the resultant mixture was stirred at a temperature of 50° C. for 1 hour. The product in the reaction mixture was analyzed by gas chromatography, and the analysis revealed the formation of 0.204 g of adamantanediacrylate (yield: 74%).

Comparative Example 2

0.168 g (1.00 mmol) of adamantanediol and 0.222 g (2.20 mmol) of triethylamine were dissolved in 2 ml of dioxane at a temperature of 50° C. To the resultant mixture was added dropwise a solution of 0.230 g (2.20 mmol) methacrylic acid chloride in dioxane (2 ml) at a temperature of 50° C. for 1 hour, and then, the resultant mixture was stirred at a temperature of 50° C. for 1 hour. The analysis by gas chromatography revealed that the product in the reaction mixture was 0.237 g of adamantane-dimethacrylate (yield: 78%).

Comparative Example 3

To 2 ml of dioxane were added 0.168 g (1.00 mmol) of adamantanediol, 0.019 g (0.10 mmol) of p-toluenesulfonic acid and 0.159 g (2.20 mmol) of acrylic acid, and the resultant mixture was stirred at a temperature of 50° C. for 8 hours. The analysis by gas chromatography revealed the formation of 0.224 g of adamantane-diacrylate (yield: 81%).

Comparative Example 4

The reaction was conducted in the same manner as in comparative example 1 except that 1 mmol of adamanetanol, 1.20 mmol of trietylamine, 1.2 mmol of acrylic acid chloride and 2 ml of dioxane were used, and 0.167 g of adamantanemonoacrylate (yield: 81%) was formed.

Comparative Example 5

The reaction was conducted in accordance with the method of The Japanese Patent Publication No. 61980/1995 (JP-B-7-61980) to obtain an adamantane monoaclylate, namely, 15 mole of anhydrousbromine and 1.6 mole of adamantane were reacted at the reflux temperature of bromine for 7 hours, surplus bromine was distilled off under reduced pressure, and after the addition of 200 ml of carbon tetrachloride (IV), the residual bromine was resolved with sodium sulfite. A white powdery 1-bromoadamantane was provided by removing organic layer, and recrystallizing the obtained crude products from methanol.

The obtained 1 mol of 1-bromoadamantane, 400 ml of 0.67 N-hydrochloric acid and 450 ml of dimethylformamide and the resultant were stirred at the reflux temperature for 1 hour. Then, the solid product was filtrated and recrystallized from n-hexane to produce a white needle 1-hydrxyadamantane.

To 200 ml of toluene were added 0.1 mole of 1-hydroxyadamantane, 0.2 mole of acrylic acid, 0.06 mole of p-toluene sulfinic acid and 0.2 mole of p-methoxyphenol, and the resultant mixture was stirred at the reflux temperature to esterify reacted while collecting the provided water to the point where the amount of produced water reached the theoretical amount. The reaction product was neutralized by 10 parts by weight of sodium hydroxide solution, and the precipitate produced was separated by filtration, and the toluene was distilled off under reduced pressure. The resultant crude product was recrystalized from n-hexane to obtain an adamantane monoacrylate.

Comparative Example 6

To 324 ml of 70% sulfuric acid was added 0.33 mole of the 1-hydroxyadamantane obtained in Comparative Example 5, and the resultant mixture was stirred at the temperature of 95° C. for 4 hours. The reaction product was poured into ice water extracted with ethanol. The water phase was neutralized by sodium hydroxide and extracted with n-butanol, then the solvent was distilled off from the extract under reduced pressure. The crude product was recrystallized from n-hexane to obtain a powderly 1,3-dihydroxyadamantane.

The esterification was conducted in the same manner as in Comparative Example 5 except that the obtained 1,3-dihydroxadamantane was used instead of using the 1-hydroxyadamantane of Comparative Example 5 to obtain an adamantane diacrylate.

Example 1

To 2 ml of dioxane were added 0.168 g (1.00 mmol) of adamantanediol, 0.040 g (0.010 mmol) of samarium iodide ($SmI_2$) and 0.216 g (2.20 mmol) of vinyl acrylate, and the resultant mixture was stirred at a temperature of 50° C. for 6 hours. The analysis by gas chromatography revealed the formation of 0.273 g of an adamantanediacrylate (yield: 99%, white solid) in the reaction mixture.

Example 2

The reaction was conducted in the same manner as in Example 1 except that 2.20 mmol of isopropenyl was used instead of the vinyl acrylate and that the reaction time was 4 hours. As a result, 0.273 g (yield: 97%, white solid) of an adamantanediacrylate was formed in the reaction mixture.

Example 3

To 2 ml of dioxane were added 0.168 g (1.00 mmol) of adamantanediol, 0.040 g (0.10 mmol) of samarium iodide ($SmI_2$) and 0.247 g (2.20 mmol) of vinyl methacrylate, and the resultant mixture was stirred at a temperature of 50° C. for 6 hours. The analysis of the product revealed that the formation of 0.292 g of an adamantanedimethachrilate (yield: 96%, white solid) in the reaction mixture.

Example 4

The reaction was conducted in the same manner as in Example 3 except that 2.20 mmol of isopropenyl methacrylate was used instead of the vinyl methacrylate and that the reaction time was shortened to 4 hours. In the reaction mixture 0.301 g of adamantanediacrylate (yield: 98%) was formed.

Example 5

To 2 ml of dioxane were added 0.168 g (1.00 mmol) of adamantanediol, 0.045 g (0.10 mmol) of di($\eta^5$-pentametylcyclopentadienyl)samarium [ $CP^*_2$ Sm(THF)$_2$ ]and 0.216 g (2.20 mmol) of vinyl acrylate, and the resultant mixture was stirred at a temperature of 50° C. for 6 hours. The analysis by gas chromatography revealed the formation of 0.271 g (yield: 98%) of an adamantanediacrylate in the reaction mixture.

Example 6

To 2 ml of dioxane were added 0.168 g (1.00 mol) of adamantanediol, 0.045 g (0.10 mmol) of $C^*_2Sm(THF)_2$ and 0.247 g (2.20 mmol) of vinyl methacrylate, and the resultant mixture was stirred at a temperature of 50° C. for 6 hours. The analysis by gas chromatography revealed the formation of 0.295 g of adamantanedimethacrylate (yield: 97%) in the reaction mixture.

Example 7

To 2 ml of dioxane were added 0.168 g (1.00 mmol) of adamantanediol, 0.045 g (0.10 mmol) of $Cp^*_2Sm$ (THF)$_2$, 0.247 g (2.20 mmol) of vinyl acrylate and 0.023 g (0.20 mmol) of cyclohexaneoxime, and the resultant mixture was stirred at a temperature of 50° C. for 4 hours. The analysis by gas chromatography revealed the formation of 0.271 g of adamantanediacrylate (yield: 98%) in the reaction mixture.

Examples 8 and 9

The reaction was conducted in the same manner as in Example 1 except that 0.1 mmol of samariumtriflate (III) (Example 8), 0.1 mmol of scandiumtriflate (Example 9) were used instead of the samarium iodide of Example 1. The results were the same as those of Example 1 (0.265 g of adamantanediacrylate (yield: 96%).

Example 10

The reaction was conducted in the same manner as in Example 1 except that 1 mmol of adamantanol, 0.1 mmol of samarium iodide, 4.5 mmol of vinyl acrylate and dioxane (2 ml) were used, and resulted in the formation of 0.204 g of adamantanemonoacrylate (yield: 99%, colorless liquid).

Example 11

The reaction was conducted in the same manner as in Example 1 except that 1 mmol of adamantanetetraol, 0.1 mmol of samarium iodide, 4.5 mmol of vinyl acrylate and dioxane (2 ml) were used, and resulted in the formation of 0.395 g of adamantanetetracrylate (yield: 95%, white solid).

And then, the reaction mixtures of Comparative Examples 1, 2 and 4, Examples 1~8 and 10 were distilled under reduced pressure to remove a solvent and a reaction agent, and the yield of the object compound was measured. And then, the products by distillation under reduced pressure were refined by being subjected to column separation (column: wako-gel C-300, elution solvent: n-hexane/ethyl acetate=8/2 (V/V)).

The refined products by column separation, those of Comparative Examples 1, 2 and 4 containing chlorine, were recrystallized twice and the content of the chlorine was reduced to 10 ppm or less. Further, the content of the chlorine in the refined products by column separation was 700 ppm in Comparative Example 1, 850 ppm in Comparative Example 2, 930 ppm in Comparative Example 4. The amount of halogen contained in each product and refined product by column separation obtained in Examples 1–10 was not more that 10 ppm, thus, no recrystalliation was occurred.

The yields (isolation yield) of the object compounds obtained by the reaction and refining are shown in Table 1.

TABLE 1

| | Yield (%) | | | |
|---|---|---|---|---|
| | In the reaction mixture | After the distillation in reduced pressure | After the separation by the column | After the recrystallization |
| Com. Ex. 1 | 74 | 68 | 64 | 49 |
| Com. Ex. 2 | 78 | 72 | 69 | 58 |
| Com. Ex. 4 | 81 | 74 | 69 | 61 |
| Ex. 1 | 97 | 94 | 91 | N.R. |
| Ex. 2 | 99 | 96 | 92 | N.R. |
| Ex. 3 | 96 | 94 | 90 | N.R. |
| Ex. 4 | 99 | 96 | 93 | N.R. |
| Ex. 5 | 98 | 95 | 91 | N.R. |
| Ex. 6 | 97 | 95 | 92 | N.R. |
| Ex. 7 | 98 | 93 | 90 | N.R. |
| Ex. 8 | 96 | 92 | 88 | N.R. |
| Ex. 10 | 99 | 98 | 95 | N.R. |

N.R.: Recrystallization is not required.

[Physical properties of polymer]

To (i) the adamantanediacrylate (Example 1, Comparative Example 6), (ii) the adamantanemonoacrylate (Example 10, Comparative Example 5), (iii) a mixture of the 50% by weight adamantaemonoacrylate (Example 10) and 50% by weight methyl methacrylate (AMA-MMA39), (iv) a mixture of the 50% by weight adamantane monoacrylate (Example 10) and 50% by weight diethylene glycol bis allylcarbonate (CR39) (AMA-CR39) and (v) methyl methacrylate (MMA) were added 0.1 part by weight of photo-polymerization initiator (benzophenone). The mixture was applied to glass plate and photo-polymerized by irradiation of ultraviolet rays.

Physical properties of the obtained polymer were measured and the results are shown in Table 2.

The properties of the polymer in the Table were measured based on the following conditions, Refractive index: measured with Abbe's refractometer NAR-L (light source Na-d, 587.6 nm), manufactured by ATAGO Co., Ltd.

Light-transmisson: ASTM-D1003

Double refraction: measured in accordance with the method of Senarmon with He-Ne laser Pencil hardness: measured with pencil hardness tester, manufactured by KANEHISA Co., Ltd.

Thermal deformation point: measured with oil-carried thermal deformation meter, manufactured by YASU-DASEIKI Co., Ltd.

Water absorption (%): soaked in boiling water at 100° C. for two hours and measured Content of the halogen (bromine): the standard solution containing 5 ppm of bromine was prepared by thinning the standard solution for atomic absorption spectrometry with pure water in order. Drew the calibration curve with the prepared standard solution, and measured with atomic absorption spectrometer (AA-6700, manufactured by SHI-MAZU Co., Ltd.).

Coefficient of polycondensation: measured the mass of the polymer before and after polymerization with a measuring cylinder in the water at 25° C.

Coefficient of polycondensation shows the coefficient of condensation, as a result of polymerization from monomer to polymer.

TABLE 2

| | Ex. 10 | Ex. 1 | AMA-MMA | AMA-CR39 | Com. Ex. 5 | Com. Ex. 6 |
|---|---|---|---|---|---|---|
| Specific gravity (g/cm$^3$) | 1.017 | 1.015 | 1.072 | 1.055 | 1.018 | 1.014 |
| Refractive index (nD$_2$O) | 1.535 | 1.537 | 1.52 | 1.52 | 1.50 | 1.51 |
| Dispersing index (%) | 53.0 | 56.3 | 56.8 | 56.1 | 51.1 | 55.8 |
| Transmittance (%) | 92 | 92 | 92 | 92 | 90 | 91 |
| Birefringence (nm) | 50> | 50> | 50> | 50> | 50< | 50< |
| Hardness of pencil | 4 H | 4 H | 3 H | 3 H | 4 H | 4 H |
| Water absorption (%) | 0.13 | 0.08 | 0.14 | 0.12 | 0.13 | 0.08 |
| Polymerization shrinking index (%) | 7.7 | 8.1 | 10.5 | 9.0 | 7.7 | 8.1 |
| Temperature of thermal Deformation (° C.) | 160 | 200< | 136 | 124 | 160 | 200< |
| Glass transition Temperature (° C.) | 178 | 200< | 155 | 140 | 178 | 200< |
| Color number | 5 | 3 | 10 | 8 | 66 | 52 |
| Content of Br (ppm) | 1> | 1> | 1> | 1> | 127 | 105 |

Preparation Example 4

A flask with side arms (50 ml) was immersed in ice water, and the pressure was reduced. Nitrogen monoxide was introduced into the flask from a gas pack (1L) and oxygen was introduced into the flask from a gas pack (1L) at the same time. The flask was filled with a reddish brown gas, and a blue liquid or solution containing mainly $N_2O_3$ was formed as the brownish red gas settled. The said introduction of nitrogen monoxide and oxygen was alternately repeated to produce about 1.5 L of a blue liquid or solution, and it was frozen with liquid nitrogen.

To 5 ml of acetate were added 1.8 g ($N_2O_3$ conversion is 0.024 mol) of a frozen blue solution, 1 mmol of adamantane and 0.05 mmol of NHPI, and the resultant mixture was reacted with stirring at a temperature of 100° C. for 10 hours to form a 1-ntroadamantane and a 1,3-dinitroadamantane.

To 25 ml of acetic acid were added 10 mmol of 1-nitroadamantane, 1 mmol of NHPI and 0.05 mmol of $V(AA)_3$, and the resultant mixture was stirred in an oxygen atmosphere at a temperature of 75° C. for 8 hours. The analysis by gas chromatography revealed the formation of 1-nitro-3-adamantanol (yield: 48%) a 1-nitro-3,5-adamantanediol (yield:19%) and a 1-nitro-3,5,7-adamantanetriol (yield:2%), converted from 1-nitroadamantane at a conversion rate of 76%. These products were analyzed by mass spectrometric analysis.

(1) 1-nitro-3-adamantanol

Light yellow solid

Mass spectrum data (fragment)

$[M]^+$: 181, $[M]^-$: 163 (—$OH_2$), $[M]^{--}$: 117(—$NO_2$)

(2) 1-nitro-3,5-adamantanediol

Light yellow solid

Mass spectrum data (fragment)

$[M]^+$: 197, $[M]^-$: 179 (—$OH_2$), $[M]^{--}$: 133(—$NO_2$)

Preparation Example 5

To 25 ml of acetic acid were added 10 mmol of adamantane, 1 mmol of NHPI and 0.005 mmol of Co $(AA)_2$. A gas pack containing a mixed gas (2 L of carbon monoxide and 0.5 L of oxygen) was connected to a reactor, and the obtain mixture was stirred at a temperature of 60° C. for 6 hours to 1-carboxyadamantane (white solid) and a 1,3-dicarboxyadamantane.

To 25 ml of acetic acid were added 10 mmol of 1-carboxyadamantane, 1 mmol of NHPI and 0.05 mmol of V $(AA)_3$, and the resultant mixture was stirred in an oxygen atmosphere at a temperature of 75° C. for 5 hours. And, as a result, the 1-carboxyadamantane was converted into a 1-carboxy-3-adamantanol (yield: 56%, white solid), a 1-carboxy-3,5-adamantanediol (yield:28%, light yellow solid), a 1-carboxy-4-adamantanone (yield: 4%) with a conversion of 99%.

Preparation Example 6

10 mmol of the 1-carboxy-3-adamantanol produced by the method of Preparation Example 5 under a nitrogen atmosphere was dissolved in 10 ml of DMF, and 15 mmol of thionyl chloride was dropped into the solution for 30 minutes. The temperature was elevated so that the solution starts its reflux at the end of dropping. After two hours of reflux, the reactant mixture was cooled, added 20 mmol of triethylamine, the temperature of the mixture was maintained at 10° C. or below, and 11 mmol of methanol was added dropwise for 30 minutes and stirred for 2 hours. And, at the result, the 1-carboxy-3-adamantanol was converted into a 1-methoxycarbonyl-3-adamantanol (yield: 95%) with a conversion of 99%.

White solid

Mass spectrum data $[M]^+$: 210

IR ($cm^{-1}$): 3350, 1730, 1130

Preparation Example 7

To 25 ml of acetic acid were added 10 mmol of adamantane, 1 mmol of NHPI and 0.05 mmol of acethylacetonatocobalt(II) ($Co(AA)_2$), and the resultant mixture was stirred in an oxygen atmosphere at a temperature of 75° C. for 6 hours. The adamantane was converted into a 1-acethyloxyadamantane (white solid) and a 1,3-diacethyloxyadamantane (white solid).

To 25 ml of acetic acid were added 10 mmol of said 1-acethyloxyadamantane, 1 mmol of NHPI and 0.05 mmol of V $(AA)_3$, and the resultant mixture was stirred in an oxygen atmosphere at a temperature of 75° C. for 8 hours. And, as a result, the 1-acethyloxyadamane was converted into a 1-acethyloxy-3-adamantanol (yield:37%), a 1-acethyloxy-3,5-adamatanediol (yield:25%) and a 1-acethyloxy-3,5,7-adamantanetriol (yield:11%) with a conversion of 89%.

(1) 1-acethyloxy-3-adamantanol

White solid

Mass spectrum data (fragment)

$[M]^+$: 210, $[M]^-$: 151 (-$OA_C$), $[M]^{--}$: 133 (—$OH_2$)

(2) 1-acethyloxy-3,5-adamantanediol

White solid

Mass spectrum data (fragment)

$[M]^+$: 226, $[M]^-$: 167 (—$OA_C$), $[M]^{--}$: 149 (—$OH_2$)

Preparation Example 8

15 mmol of aluminiumlitium hydroxide was suspended in 15 ml of tetrahydrofuran (THF) in a nitrogen atmosphere. To the solution was slowly added 10 mmol of the 1-carboxy-3-adamantanol obtained in Preparation Example 5 while the temperature of the solution was maintained at less than 10° C. or below by ice water bath. After the temperature of the mixture was raised to room temperatures, the mixture was refluxed for 16 hours. And, as the result, the 1-carboxy-3-adamantanol was converted into a 1-hydroxymethyl-3-adamantanol (yield: 95%) with a conversion of 99%.

White solid

Mass spectrum data $[M]^+$: 182

IR ($cm^{-1}$): 3370, 1380, 1120

Preparation Example 9

An autocrave was charged with 10 ml of methanol were added 10 mmol of the 1-nitro-3-adamantanol obtained by the method of Preparation Example 4, 5% Pd-C (10 mol % as Pd, relative to a substrate) and 1 ml of hydrochloric acid, and the mixture was stirred in a hydrogen atmosphere at a temperature of 80° C. for 2 hours. And, as a result, the 1-nitro-3-adamantanol was converted into a 1-amino-3-adamantanol (yield:95%) with a conversion of 99%.

Light yellow solid

Mass spectrum data $[M]^+$: 167

IR ($cm^{-1}$): 3370, 3340, 1620, 1360

11 mmol of acetyl chloride and 12 mmol of triethylamine were dissolved in 2 ml of THF in a nitrogen atmosphere, and to the reactant solution was dropped 10 mmol of DMF (10 ml) solution with said 1-amino-3-adamantanol at a temperature of 40° C. for 30 minutes. Then, the reactant mixture was stirred at a temperature of 40° C. for 3 hours. And, as a result, the 1-amino-3-adamantanol was converted into a 1-acetylamino-3-adamantanol (yield: 95%) with a conversion of 99%.

Light yellow solid

Mass spectrum data [M]$^+$: 209

IR (cm$^{-1}$): 3350, 1670, 690

Preparation Example 10

To 25 ml of acetic acid were added 10 mmol of 1,3-adamantanediol, 1 mmol of NHPI and 0.05 mmol of acetylacetonatovanadium (III) (V(AA)$_3$), and the resultant mixture was stirred in an oxygen atmosphere at a temperature of 75° C. for 6 hours. And, as a result, the 1,3-adamantanediol was converted into a 1,3,5-adamantanetriol (yield: 80%) with a conversion of 99%.

White solid

Mass spectrum data [M]$^+$: 184

IR (cm$^{-1}$): 3320, 1320, 1170

Preparation Example 11

A flask with side arms (50 ml) was immersed in ice water, and the pressure was reduced. Oxygen was introduced into the flask from the gas pack (1L) while nitrogen monoxide was introduced into the flask from the gas pack (1L), flask was filled with a brownish red gas and a blue solution whose principal ingredient was N$_2$O$_3$ was produced as the brownish red gas was precipitated. The said introductions of nitrogen monoxide and oxygen were repeated so as to produce about 1.5 L of blue solution, and the blue solution was frozen with liquid nitrogen.

To 5 ml of acetic acid were added 1.8 g (0.024 mol, in terms of N$_2$O$_3$) of the frozen blue solution, 1 mmol of 1,3-adamantanediol and 0.05 mmol of NHPI, and the resultant mixture was reacted with stirring at a temperature of 100° C. for 10 hours, and, as a result, the 1,3-adamantanediol was converted into a 1-nitro-3,5-adamantanediol (yield:80%) with a conversion of 99%.

Light yellow solid

Mass spectrum data [M]$^+$: 213

IR (cm$^{-1}$): 3320, 1320, 1170

Preparation Example 12

To 25 ml of acetic acid were added 10 mmol of 1,3-adamantanediol, 1 mmol of NHPI and 0.005 mmol of Co (AA)$_2$, a gas pack containing a mixed gas (2 lit. of carbon monoxide and 0.5 lit. of oxygen; pressure:5 kg/cm$^2$) was connected with the reactor, and the resultant mixture was stirred at a temperature of 60° C. for 6 hours. And, as a result, the 1,3-adamantanediol was converted into a 1-carboxy-3,5-adamantanediol (yield: 80%) with a conversion of 99%.

White solid

Mass spectrum data [M]$^+$: 212

IR (cm$^{-1}$): 3320, 1320, 1170

Example 12

The reaction was conducted in the same manner as in Example 2 except that 1.00 mmol of the 1-nitro-3-adamantanol obtained by the method of Preparation Example 4 and 1.10 mmol of isopropenil acrylate were used instead of the adamantanediol, and, as a result, a 1-acryloiloxy-3-nitroadamantane was obtained with a yield of 99%.

Light yellow solid

Mass spectrum data [M]$^+$: 251

IR (cm$^{-1}$): 1730, 1560, 1450, 1120

Example 13

The reaction was conducted in the same manner as in Example 4 except that 1.00 mmol of the 1-nitro-3-adamantanol obtained by the method of Preparation Example 4 and 1.10 mmol of isopropenil methacrylate were used instead of the adamantanediol, and, as a result, a 1-methacryloiloxy-3-nitroadamantane was obtained with a yield of 99%.

Light yellow solid

Mass spectrum data [M]$^+$: 265

IR (cm$^{-1}$): 1720, 1550, 1460, 1140

Example 14

The reaction was conducted in the same manner as in Example 2 except that 1.00 mmol of the 1-carboxy-3-adamantanol obtained by the method of Preparation Example 5 and 1.10 mmol of isopropenil acrylate were used instead of the adamantanediol, and, as a result, a 1-acryloiloxy-3-carboxyadamantane was obtained with a yield of 99%.

White solid

Mass spectrum data [M]$^+$: 250

IR (cm$^{-1}$): 3030, 1670, 1620, 1430

Example 15

The reaction was conducted in the same manner as in Example 4 except that 1.00 mmol of the 1-carboxy-3-adamantanol obtained by the method of Preparation Example 5 and 1.10 mmol of isopropenil methacrylate were used instead of the adamantanediol, and, as a result, a 1-carboxy-3-methacryloiloxyadamantane was obtained with a yield of 99%.

White solid

Mass spectrum data [M]$^+$: 264

IR (cm$^{-1}$): 3020, 1670, 1630, 1450

Example 16

The reaction was conducted in the same manner as in Example 2 except that 1.00 mmol of the 1-methoxycarbonyl-3-adamantanol obtained by the method of Preparation Example 6 and 1.10 mmol of isopropenil acrylate were used instead of the adamantanediol, and, as a result, a 1-acryloyloxy-3-methoxycarbonyladamantane was obtained with a yield of 99%.

Colorless viscid liquid

Mass spectrum data [M]$^+$: 264

IR (cm$^{-1}$): 1620, 1440, 1240, 1030

Example 17

The reaction was conducted in the same manner as in Example 4 except that 1.00 mmol of the 1-methoxycarbonyl-3-adamantanol obtained by the method of Preparation Example 6 and 1.10 mmol of isopropenyl methacrylate were used instead of the adamantanediol, and, as a result, a 1-methacryloyloxy-3-methoxycarbonyladamantane was obtained with a yield of 99%.

Colorless viscid liquid

Mass spectrum data [M]$^+$: 278

IR (cm$^{-1}$): 1620, 1460, 1240, 1010

Example 18

The reaction was conducted in the same manner as in Example 2 except that 1. 10 mmol of isopropenyl acrylate, and, as a result, a 1-acryloyloxy-3-adamantanol was obtained with a yield of 90%.

White solid

Mass spectrum data [M]$^+$: 222

IR (cm$^{-1}$): 3320, 1620, 1440, 1240

Example 19

The reaction was conducted in the same manner as in Example 4 except that 1.10 mmol of isopropenyl methacrylate, and, as a result, a 1-methacryloyloxy-3-adamantanol was obtained with a yield of 90%.

White solid

Mass spectrum data [M]$^+$: 236

IR (cm$^{-1}$): 3310, 1620, 1450, 1220

Example 20

The reaction was conducted in the same manner as in Example 2 except that 1.00 mmol of the 1-acetyloxy-3-adamantanol obtained by the method of Preparation Example 7 and 1.10 mmol of isopropenyl acrylate were used instead of the adamantanediol, and, as a result, a 1-acetyloxy-3-acryloyloxyadamantane was obtained with a yield of 99%.

White solid

Mass spectrum data [M]$^+$: 264

IR (cm$^{-1}$): 1660, 1450, 1240, 1010

Example 21

The reaction was conducted in the same manner as in Example 4 except that 1.00 mmol of the 1-acetyloxy-3-adamantanol obtained by the method of Preparation Example 7 and 1.10 mmol of isopropenyl methacrylate were used instead of the adamantanediol, and, as a result, a 1-acetyloxy-3-methacryloyloxyadamantane was obtained with a yield of 99%.

White liquid

Mass spectrum data [M]$^+$: 278

IR (cm$^{-1}$): 1660, 1470, 1240, 1030

Example 22

The reaction was conducted in the same manner as in Example 2 except that 1.00 mmol of the 1-hydroxymethyl-3-adamantanol obtained by the method of Preparation Example 8 and 1.10 mmol of isopropenyl acrylate were used instead of the adamantanediol, and, as a result, (1) 1-acryloiloxy-3-hydroxymethladamantane and (2) 1-acryloyloxymethyl-3-adamantanol were obtained.

(1) 1-acryloyloxy-3-hydroxymethyladamantane

White solid

Mass spectrum data [M]$^+$: 236

IR (cm$^{-1}$): 3330, 1490, 1440, 720

(2) 1-acryloyloxymethyl-3-adamantanol

White solid

Mass spectrum data [M]$^+$: 236, [M]$^-$: 218, [M]$^{--}$: 191, [M]$^{---}$: 147, [M]$^{----}$: 133

Example 23

The reaction was conducted in the same manner as in Example 4 except that 1.00 mmol of the 1-hydroxymethyl-3-adamantanol obtained by the method of Preparation Example 8 and 1.10 mmol of isopropenyl 4 methacrylate were used instead of the adamantanediol, and, as a result, a 1-hydroxymethyl-3-meyhacryloyloxyadamantane was obtained with a yield of 90%.

White solid

Mass spectrum data [M]$^+$: 250

IR (cm$^{-1}$): 3320, 1500, 1420, 750

Example 24

The reaction was conducted in the same manner as in Example 2 except that 1.00 mmol of the 1-acetylamino-3-adamantanol obtained by the method of Preparation Example 9 and 1.10 mmol of isopropenyl acrylate were used instead of the adamantanediol, and, as a result, a 1-acetylamino-3-acryloyloxyadamantane was obtained with a yield of 99%.

Light yellow solid

Mass spectrum data [M]$^+$: 263

IR (cm$^{-1}$): 3320, 1650, 1420, 1200

Example 25

The reaction was conducted in the same manner as in Example 4 except that 1.00 mmol of the 1-acetylamino-3-adamantanol obtained by the method of Preparation Example 9 and 1.10 mmol of isopropenyl methacrylate were used instead of the adamantanediol, and, as a result, a 1-acetylamino-3-methacryloyloxyadamantane was obtained with a yield of 99%.

Light yellow solid

Mass spectrum data [M]$^+$: 277

IR (cm$^{-1}$): 3320, 1660, 1420, 1220

Example 26

The reaction was conducted in the same manner as in Example 2 except that 1.00 mmol of the 1,3,5-adamantanetriol obtained by the method of Preparation Example 9 and 1.10 mmol of isopropenyl acrylate were used instead of the adamantanediol, as a result, a 1-acryloyloxy-3,5-adamantanediol was obtained with a yield of 90%.

White liquid

Mass spectrum data [M]$^+$: 238

IR (cm$^{-1}$): 3320, 1620, 1320, 1140

Example 27

The reaction was conducted in the same manner as in Example 26 except that 2.20 mmol of isopropenyl acrylate was used, and, as a result, a 1,3-bis(acryloyloxy)-5-adamantanol was obtained with a yield of 85%.

White liquid

Mass spectrum data [M]$^+$: 292

IR (cm$^{-1}$): 3300, 1610, 1310, 1150

Example 28

The reaction was conducted in the same manner as in Example 26 except that 3.30 mmol of isopropenyl acrylate was used, and, as a result, a 1,3,5-tris(acryloyloxy) adamantane was obtained with a yield of 95%.

White liquid

Mass spectrum data [M]$^+$: 346

IR (cm$^{-1}$): 1620, 1320, 1140

Example 29

The reaction was conducted in the same manner as in Example 4 except that 1.00 mmol of the 1,3,5- adamantanetriol obtained by the method of Preparation Example 10 and 1.10 mmol of isopropenyl methacrylate were used instead of the adamantanediol, and, as a result, a 1-methacryloyloxy-3,5-adamantanediol was obtained with a yield of 90%.

White liquid

Mass spectrum data $[M]^+$: 252

IR $(cm^{-1})$: 3320, 1610, 1390, 1120

Example 30

The reaction was conducted in the same manner as in Example 29 except that 2.20 mmol of isopropenyl methacrylate was used, and, as a result, a 1,3-bis(methacryloyloxy)-5-adamantanol was obtained with a yield of 85%.

White liquid

Mass spectrum data $[M]^+$: 320

IR $(cm^{-1})$: 3330, 1610, 1360, 1150

Example 31

The reaction was conducted in the same manner as in Example 29 except that 3.30 mmol of isopropenyl methacrylate was used, and, as a result, a 1,3,5-tris(methacryloyloxy) adamantane was obtained with a yield of 95%.

White liquid

Mass spectrum data $[M]^+$: 388

IR $(cm^{-1})$: 1640, 1470, 1320, 1140

Example 32

The reaction was conducted in the same manner as in Example 2 except that 1.00 mmol of the 1-nitro-3,5-adamantanediol obtained by the method of Preparation Example 11 and 2.20 mmol of isopropenyl acrylate were used instead of the adamantanediol, and, as a result, a 1,3-bis(acryloyloxy)-5-nitroadamantane was obtained with a yield of 99%.

Light yellow solid

Mass spectrum data $[M]^+$: 321

IR $(cm^{-1})$: 1560, 1460, 1360, 1140

Example 33

The reaction was conducted in the same manner as in Example 4 except that 1.00 mmol of the 1-nitro-3,5-adamantanediol obtained by the method of Preparation Example 11 and 2.20 mmol of isopropenyl methacrylate were used instead of the adamantanediol, as a result, a 1,3-bis(methacryloyloxy)-5-nitroadamantane was obtained with a yield of 99%.

Light yellow solid

Mass spectrum data $[M]^+$: 349

IR $(cm^{-1})$: 1570, 1440, 1360, 1120

Example 34

The reaction was conducted in the same manner as in Example 2 except that 1.00 mmol of the carboxy-3,5-adamantanediol obtained by the method of Preparation Example 11 and 2.20 mmol of isopropenyl acrylate were used instead of the adamantanediol, and, as a result, a 1,3-bis(acryloyloxy)-5-carboxyadamantane was obtained with a yield of 99%.

White solid

Mass spectrum data $[M]^+$: 240

IR $(cm^{-1})$: 3370, 1470, 1320, 1140

Example 35

The reaction was conducted in the same manner as in Example 4 except that 1.00 mmol of the 1-carboxy-3,5-adamantanediol obtained by the method of Preparation Example 12 and 2.20 mmol of isopropenyl methacrylate were used instead of the adamantanediol, and, as a result, a 1,3-bis(methacryloyloxy)-5-carboxyadamantane was obtained with a yield of 99%.

White solid

Mass spectrum data $[M]^+$: 268

IR $(cm^{-1})$: 3350, 1450, 1320, 1130

Example 36

(1) The oxidization in an oxygen atmosphere was conducted in the same manner as in Preparation Example 1 except that 1,3-dicarboxyadamantane was used instead of the adamantane and, as a result, a 1,3-dicarboxy-5-adamantanol (yield: 35%, white solid) and a 1,3-dicarboxy-5,7-dihydroxyadamantane (yield: 37%, white solid) were obtained with a conversion of 91%.

(2) To 2 mL of dioxane were added 1.00 mmol of 1,3-dicarboxy-5-adamantanol, 0.10 mmol of samarium iodide ($SmI_2$), 2.20 mmol of isopropenyl acrylate, and the resultant mixture was stirred at a temperature of 50° C. for 4 hours. The analysis by gas chromatography showed the formation of a 1,3-dicarboxy-5-acryloyloxyadamantane (yield: 82%, white solid) in the reaction mixture.

Mass spectrum data $[M]^+$: 294, $[M]^-$: 223, $[M]^{--}$: 178, $[M]^{---}$: 133

(3) The reaction was conducted in the same manner as said (2) except that 1,3-dicarboxy-5,7-dihydroxyadamantane was used instead of the 1,3-dicarboxy-5-adamantanol, and, as a result, a 1,3-dicarboxy-5-acryloyloxy-7-adamantanol (yield: 86%, white solid) was obtained.

Mass spectrum data $[M]^+$: 310, $[M]^-$: 292, $[M]^{--}$: 221, $[M]^{---}$: 176

Example 37

(1) The oxidization under an oxygen atmosphere was conducted in the same manner as in Preparation Example 1 except that 1,3-tricarboxyadamantane was used instead of the adamantane, and, as a result, a 1,3,5-tricarboxy-7-adamantanol (yield: 57%, white solid) was obtained with a conversion of 62%. The 1,3,5-tricarboxyadamantane was obtained in the same manner as in Preparation Example 5 except that the reaction time was 12 hours and the temperature was 80° C.

(2) The reaction was conducted in the same manner as the step of Example 36 (2) except that 1,3,5-tricarboxy-7-adamantanol was used instead of the 1,3-dicarboxy-5-adamantanol, and, as a result, a 1,3,5-tricarboxy-7-acryloiloxyadamantane (yield: 76%, white solid) was obtained.

Mass spectrum data $[M]^+$: 338, $[M]^-$: 267, $[M]^{--}$: 222, $[M]^{---}$: 177

Example 38

(1) The oxidization in an oxygen atmosphere was conducted in the same manner as in Preparation Example 1 except that 1-carboxyadamantane was used instead of the adamantane, and as a result, a 1-carboxy-3,5-dihydroxyadamantane (yield: 44%, white solid) and a 1-carboxy-3,5,7-trihydroxyadamantane (yield: 34%, white solid) were obtained with a conversion of 98%.

(2) The reaction was conducted in the same manner as the step of Example 36 (2) except that 1-carboxy-3,5-dihydroxyadamantane was used instead of the 1,3-dicarboxy-5-adamantanol, and, as a result, a 1-carboxy-3-hydroxy-5-acryloyloxyadamantane (yield: 84%, white solid) was obtained.

Mass spectrum data $[M]^+$: 266, $[M]^-$: 248, $[M]^{--}$: 177, $[M]^{---}$: 132

(3) The reaction was conducted in the same manner as said (2) except that 1-carboxy-3,5,7-trihydroxyadamantane was used instead of the 1-carboxy-3,5-dihydroxyadamantane, and, as a result, a 1-carboxy-3,5-dihydroxy-7-acryloyloxyadamantane (yield: 81%, white solid) was produced.

Mass spectrum data $[M]^+$: 282, $[M]^-$: 264, $[M]^{--}$: 246, $[M]^{--}$: 175

Example 39

(1) The oxidization in an oxygen atmosphere was conducted in the same manner as in Preparation Example 1 except that 1,3,5-trihydroxyadamantane was used instead of the adamantane of Preparation Example 1, and, as a result, a 1,3,5,7-tetrahydroxyadamantne (yield: 62%) with a conversion of 87%.

(2) The reaction was conducted in the same manner as the step of Example 36 (2) except that 1,3,5,7-tetrahydroxyadamantane was used instead of the 1,3-dicarboxy-5-adamantanol, and, as a result, a 1,3,5-trihydroxy-7-acryloyloxyadamantane (yield: 83%, white solid) was obtained.

Mass spectrum data $[M]^+$: 254, $[M]^-$: 236, $[M]^{--}$: 218, $[M]^{---}$: 200

Example 40

(1) The oxidization in an oxygen atmosphere was conducted in the same manner as in Preparation Example 1 except that 1-acetyladamantane was used instead of the adamantane, and, as a result, a 1-acetyl-3-hydroxyadamantane (yield: 46%, white solid) and a 1-acetyl-3,5-dihydroxyadamantane (yield: 33%, white solid) were obtained with a conversion of 98%.

(2) The reaction was conducted in the same manner as the step of Example 36 (2) except that 1-acetyl-3-hydroxyadamantane was used instead of the 1,3-dicarboxy-5-adamantanol, and, as a result, a 1-acety-3-acryloyloxyadamantane (yield: 97%, white solid) was obtained.

Mass spectrum data $[M]^+$: 248, $[M]^-$: 177, $[M]^{--}$: 162, $[M]^{---}$: 133

(3) The reaction was conducted in the same manner as said (2) except that 1-acetyl-3,5-dihyroxyadamantane was used instead of the 1-acetyl-3-hydroxyadamantane, and, as a result, a 1-acetyl-3-hydroxy-5-acryloyloxyadamantane (yield: 84%, white solid) was obtained.

Mass spectrum data $[M]^+$: 264, $[M]^-$: 246, $[M]^{--}$: 175, $[M]^{---}$: 160

Example 41

(1) The oxidization in an oxygen atmosphere was conducted in the same manner as in Preparation Example 1 except that 2-oxoadamantane (white solid) was used instead of the adamantane, and, as a result, a 1-hydroxyadamantane-2-one (yield: 36%, white solid), a 1-hydroxyadamantane-4-one (yield: 30%, white solid) and a 1,3-dihydroxyadamantane-4-one (yield: 22%, white solid) were obtained with a conversion of 94%.

(2) The reaction was conducted in the same manner as the step of Example 36 (2) except that 1-hydroxyadamantane-2-one was used instead of the 1,3-dicarboxy-5-adamantanol, and, as a result, a 1-acryloyloxyadamantane-2-one (yield: 94%, white solid) was obtained.

Mass spectrum data $[M]^+$: 220, $[M]^-$: 149

(3) The reaction was conducted in the same manner as said (2) except that 1-hydroxyadamantane-4-one was used instead of the 1-hydroxyadamantane-2-one, and, as a result, a 1-acryloyloxyadamantane-4-one (yield: 95%, white solid) was obtained.

Mass spectrum data $(M]^+$: 220, $[M]^-$: 149

(4) The reaction was conducted in the same manner as said (2) except that 1,3-dihydroxyadamantane-4-one was used instead of the 1-hydroxyadamantane-2-one, and, as a result, a 1-acryloyloxy-3-hydroxyadamantane-4-one (yield: 87%, white solid) was produced.

Mass spectrum data $[M]^+$: 236, $[M]^-$: 218, $[M]^{--}$: 147

Example 42

(1) The oxidization in an oxygen atmosphere was conducted in the same manner as in Preparation Example 1 except that 1,3-dimethyladamantane was used instead of the adamantane, and, as a result, a 1,3-dimethyl-5,7-dihydroxyadamantane (yield: 44%, white solid) and a 1,3-dimethyl-5-hydroxyadamantane (yield: 34%, white solid) were obtained with a conversion of 99%.

(2) The reaction was conducted in the same manner as the step of Example 36 (2) except that 1,3-dimethyl-5,7-dihydroxyadamantane was used instead of the 1,3-dicarboxy-5-adamantanol, and, as a result, a 1,3-dimethyl-5-hydroxy-7-acryloyloxyadamantane (yield: 87%, white solid) was obtained.

Mass spectrum data $[M]^+$: 250, $[M]^-$: 232, $[M]^{--}$: 161, $[M]^{---}$: 146

(3) The reaction was conducted in the same manner as said (2) except that 1,3-dimethyl-5-hydroxyadamantane was used instead of the 1,3-dimethyl-5,7-dihydroxyadamantane, and, as a result, a 1,3-dimethyl-5-acryloyloxyadamantane (yield: 96%, colorless liquid) was produced.

Mass spectrum data $[M]^+$: 234, $[M]^-$: 163, $[M]^{--}$: 148, $[M]^{---}$: 133

Example 43

(1) The oxidization in an oxygen atmosphere was conducted in the same manner as in Preparation Example 1 except that 1-methoxycarbonyladamantane was used instead of the adamantane, and, as a result, a 1-methoxycarbonyl-3-hydroxyadamantane (yield: 42%) and a 1-methoxycarbonyl-3,5-hydroxyadamantane (yield : 33%) were obtained with a conversion of 91%.

(2) The reaction was conducted in the same manner as the step of Example 36 (2) except that 1-methoxycarbonyl-3-hydroxyadamantane was used instead of the 1,3-dicarboxy-5-adamantanol, and, as a result, a 1-methoxycarbonyl-3-acryloyloxyadamantane (yield: 87%, white solid) was obtained.

Mass spectrum data $[M]^+$: 267, $[M]^-$: 193, $[M]^{--}$: 148

(3) The reaction was conducted in the same manner as said (2) except that 1-methoxycarbonyl-3,5-hydroxyadamantane was used instead of the 1-methoxycarbonyl-3-hydroxyadamantane, and, as a result, a 1-methoxycarbonyl-3-hydroxy-5-acryloyloxyadamantane (yield: 84%, white solid) was produced.

Mass spectrum data $[M]^+$: 280, $[M]^-$: 262, $[M]^{--}$: 191, $[m]^{---}$: 146

What is claimed is:

1. A process for producing a polymerizable adamantane derivative shown by the following formula (1):

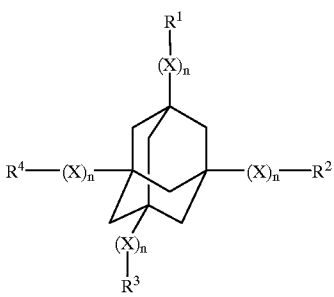

(1)

wherein $R^1$, $R^2$, $R^3$ and $R^4$ independently represent at least one substituent selected from a non-reactive atom, a non-reactive group, and a polymerizable unsaturated group, and at least one member selected from $R^1$, $R^2$, $R^3$ and $R^4$ is a polymerizable unsaturated group; X represents a connecting group comprising an ester group or an amide group, n denotes 0 or 1, and X may be different from each other according to $R^1$, $R^2$, $R^3$ and $R^4$, with the proviso that n is 0 when $R^1$, $R^2$, $R^3$ or $R^4$ is a non-reactive atom and a non-reactive group, and the binary carbon atom constituting the adamantane skeleton may have an oxo group; which comprises subjecting a compound shown by the following formula (1a):

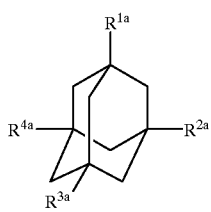

(1a)

wherein $R^{1a}$, $R^{2a}$, $R^{3a}$ and $R^{4a}$ independently represent at least one substituent selected from a non-reactive atom, a non-reactive group, a hydroxyl group, a hydroxymethyl group, a carboxyl group, an amino group and a reactive group derived therefrom, and at least one member selected from $R^{1a}$, $R^{2a}$, $R^{3a}$ and $R^{4a}$ is a hydroxyl group, a hydroxymethyl group, a carboxyl group, an amino group or a reactive group derived therefrom, and the binary carbon atom constituting the adamantane skeleton may have an oxo group;

and at least one compound selected from an alcohol having a polymerizable unsaturated bond, a carboxylic acid having a polymerizable unsaturated bond, an amine having a polymerizable unsaturated bond and a reactive derivative thereof to an esterification reaction or amidation reaction in the presence of a catalyst comprising a compound containing a Group 3A element of the Periodic Table of Elements.

2. A process for producing a polymerizable adamantane derivative according to claim 1, wherein said polymerizable unsaturated group has at least one polymerizable unsaturated double bond selected from vinyl group, isopropenyl group and allyl group.

3. A process for producing a polymerizable adamantane derivative according to claim 1, wherein said X denotes an ester bond and at least one group selected from $R^1$, $R^2$, $R^3$ and $R^4$ has a vinyl group or an isopropenyl group.

4. A process for producing a polymerizable adamantane derivative according to claim 1, wherein said adamantane derivative in which at least one group selected from $R^{1a}$, $R^{2a}$, $R^{3a}$ and $R^{4a}$ is a hydroxyl group or a reactive group derived therefrom is subjected to an esterification reaction with acrylic acid, methacrylic acid and a derivative thereof.

5. A process for producing a polymerizable adamantane derivative according to claim 1, wherein said compound containing a Group 3A element of the Periodic Table of Elements comprises a compound containing a rare earth element.

6. A process for producing a polymerizable adamantane derivative according to claim 5, wherein said compound containing a rare earth element is at least one member selected from a scandium compound, a lanthanum compound an ytterbium compound, a gadolinium compound and a samarium compound.

7. A process for producing a polymerizable adamantane derivative according to claim 5, wherein said compound containing a rare earth element is a di- or trivalent samarium compound.

8. A process for producing a polymerizable adamantane derivative according to claim 1, wherein said carboxylic acid having a polymerizable unsaturated bond, and said reactive derivative thereof is at least one member selected from the group consisting of an organic carboxylic acid having an α,β-ethylenically unsaturated double bond or triple bond or an acid halide thereof, a lower $Cl_{1-4}$alkyl ester of an organic carboxylic acid and a $C_{2-4}$alkenyl ester of an organic carboxylic acid.

9. A process for producing a polymerizable adamantane derivative according to claim 1, wherein said adamantane having 1 to 4 of hydroxyl group in the molecule, is allowed to react in the presence of a compound containing a rare earth element with at least one compound selected from the group consisting of an organic carboxylic acid having an α,β-ethylenically unsaturated double bond or an acid halide thereof, a $C_{1-4}$ lower alkyl ester of an organic carboxylic acid and a $C_{2-4}$ lower alkenyl ester of an organic carboxylic acid.

10. A process for producing a polymerizable adamantane derivative according to claim 1, which comprises subjecting said adamantane derivative to at least one step among the following oxidation step (i), carboxylation step (ii), and nitration step (iii):

(i) an oxidation step using oxygen in the presence of a catalyst comprising an imide compound shown by the following formula (2):

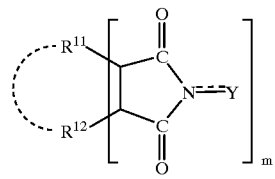

(2)

wherein $R^{11}$ and $R^{12}$ are the same or different, each representing a hydrogen atom, a halogen atom, an alkyl group, an aryl group, a cycloalkyl group, a hydroxyl group, an alkoxy group, a carboxyl group, an alkoxycarbonyl group or an acyl group; $R^{11}$ and $R^{12}$ may bond together to form a double bond, an aromatic or non-aromatic ring; Y represents an oxygen atom or a hydroxyl group; and m denotes an integer of 1 to 3;

(ii) a carboxylation step using carbon monoxide and oxygen in the presence of the catalyst comprising the imide compound shown by the formula (2);

(iii) at least one nitration step among the following (iiia), (iiib), and (iiic):

(iiia) a nitration step using a nitrogen oxide in the presence of the catalyst comprising the imide compound shown by the formula (2);

(iiib) a nitration step using at least one nitrogen oxide selected from dinitrogen oxide and nitrogen monoxide with oxygen; and (iiic) a nitration step using nitrogen dioxide;

to form a compound to which at least one reactive group selected from hydroxyl group, carboxyl group, and nitro group is introduced and subjecting the compound to said esterification or amidation reaction;

wherein the adamantane derivative is represented by said formula (1a), $R^{1a}$, $R^{2a}$, $R^{3a}$ and $R^{4a}$ therein may be the same or differently hydrogen atoms, non-reactive atoms, and non-reactive groups and at least one member among $R^{1a}$, $R^{2a}$, $R^{3a}$ and $R^{4a}$ is a hydrogen atom.

11. A process for producing a polymerizable adamantane derivative according to claim 10, wherein after at least one step of said carboxylation step (ii) and nitration step (iii), a reaction product is further subjected to a reduction step to form at least one group selected from a hydroxymethyl group and an amino group.

12. A process for producing a polymerizable adamantane derivative according to claim 10, wherein said catalyst comprises the imide compound shown by the formula (2) and a co-catalyst.

13. A process for producing a polymerizable adamantane derivative according to claim 12, wherein said co-catalyst is a compound containing at least one element selected from the group consisting of Group 3A elements, Group 4A elements, Group 5A elements, Group 6A elements, Group 7A elements, Group 8 elements and Group 1B elements of the Periodic Table of Elements.

14. A polymerizable adamantane derivative shown by the following formula:

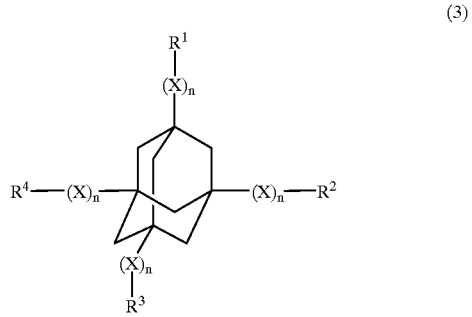

(3)

wherein $R^1$, $R^2$, $R^3$ and $R^4$ may be the same or different each representing at least one substituent selected from a non-reactive atom, a non- reactive group, and a polymerizable unsaturated group, and at least one selected from $R^1$, $R^2$, $R^3$ and $R^4$ is a polymerizable unsaturated group;

X denotes a —OC(=O)— group in which the left end thereof is intended as a moiety bound to an adamantane back bone;

n denotes 0 or 1 with the proviso that n is 0 when $R^1$, $R^2$, $R^3$ or $R^4$ is a non-reactive atom or a non-reactive group; and at least one member selected from $R^1$, $R^2$, $R^3$ and $R^4$ is a non-reactive group selected from the group consisting of nitro group, amino group which may be protected by a protective group or an N-substituted amino group which may be protected by a protective group, carboxyl group which may be protected by a protective group and hydroxymethyl group which may be protected by a protective group, and the binary carbon atom constituting the adamantane skeleton may have an oxo group.

* * * * *